United States Patent [19] [11] Patent Number: 6,153,749
Kodama et al. [45] Date of Patent: Nov. 28, 2000

[54] PROCESS FOR THE PREPARATION OF ACYLATED HEXAAZAISOWURTZITANE DERIVATIVES

[75] Inventors: Tamotsu Kodama; Haruyuki Minoura; Nobuhisa Miyake; Setsuo Yamamatsu, all of Kurashiki; Tsutomu Katsumata, Yokohama, all of Japan

[73] Assignee: Asahi Kasei Kogyo Kabushiki Kaisha, Osaka, Japan

[21] Appl. No.: 09/214,439

[22] PCT Filed: Oct. 14, 1997

[86] PCT No.: PCT/JP97/03695

§ 371 Date: Jan. 11, 1999

§ 102(e) Date: Jan. 11, 1999

[87] PCT Pub. No.: WO98/16529

PCT Pub. Date: Apr. 23, 1998

[30] Foreign Application Priority Data

Oct. 14, 1996 [JP] Japan ................................. 8-270739
Apr. 17, 1997 [JP] Japan ................................. 9-114213

[51] Int. Cl.$^7$ ................................................. C07D 259/00
[52] U.S. Cl. ............................ 540/556; 540/554; 149/92
[58] Field of Search ..................................... 540/554, 556

[56] References Cited

U.S. PATENT DOCUMENTS 5,693,794 12/1997 Nielsen .................................. 540/554

FOREIGN PATENT DOCUMENTS

WO96/23792 8/1996 WIPO .
WO97/20785 6/1997 WIPO .

OTHER PUBLICATIONS

Bellamy et al., Tetrahedron vol. 51 No. 16, Laycs 4711–22 (1995).
Reductive Debenzylation of Hexabenzylbexaazaisowurtzitane, by Anthony J. Bellamy, "Tetrahedron" vol. 51, No. 16, 4711–22 (1995).

Primary Examiner—Mukund J. Shah
Assistant Examiner—Pavanaram K Sripada
Attorney, Agent, or Firm—Finnegan, Henderson, Farabow, Garrett & Dunner, L.L.P.

[57] ABSTRACT

Disclosed is a method for producing an acyl group-containing hexaazaisowurtzitane derivative represented by the following formula (1), $$WA_nH_{(6-n)} \qquad (1)$$

wherein n represents an integer of 4 or 6, each A independently represents an acyl group having 1 to 10 carbon atoms, H represents a hydrogen atom, and W represents a hexavalent hexaazaisowurtzitane residue represented by the following formula (2):

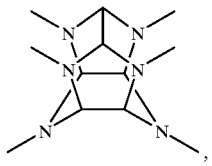

(2)

which comprises: providing a composition system comprising a mixed solvent of a first solvent and a second solvent respectively having high and low dissolving abilities for the desired compound, wherein the mixed solvent has the desired compound dissolved therein; and removing the first solvent having a high dissolving ability from the composition system to thereby deposit crystals of the desired compound. The desired compound, which is useful as a precursor of high performance explosive additive, i.e., hexanitrohexaazaisowurtzitane, can be easily produced in high purity form in high yield and at low cost.

26 Claims, No Drawings

PROCESS FOR THE PREPARATION OF ACYLATED HEXAAZAISOWURTZITANE DERIVATIVES

BACKGROUND OF THE INVENTION

1. Field of the Invention

The present invention relates to a method for producing an acyl group-containing hexaazaisowurtzitane derivative which is useful as a precursor of a hexanitrohexaazaisowurtzitane derivative which can be used for improving the performance of conventional explosives. More particularly, the present invention is concerned with a method for producing an acyl group-containing hexaazaisowurtzitane derivative, which comprises: providing a composition system comprising a mixed solvent of a first solvent and a second solvent respectively having high and low dissolving abilities for the desired compound, wherein the mixed solvent has the desired compound dissolved therein; and (α) removing the first solvent having a high dissolving ability from the composition system to thereby deposit crystals of the desired compound, or (α') causing the above-mentioned composition system to undergo a phase separation into a first solvent phase containing the desired compound dissolved therein and a second solvent phase containing no desired compound or containing only a small amount of the desired compound dissolved therein, followed by removal of the first solvent from the first solvent phase to thereby deposit crystals of the desired compound.

The method of the present invention is commercially advantageous in that it can be used for producing an acyl group-containing high-purity hexaazaisowurtzitane derivative in high yield and at low cost.

2. Prior Art

As a conventional method for producing an acyl group-containing hexaazaisowurtzitane derivative, a method is known in which a hexakis(arylmethyl)hexaazaisowurtzitane is subjected to reductive dearylmethylation in the presence of an acylating agent to thereby obtain a hexaazaisowurtzitane derivative, which has an acyl group and having at least one type group or atom selected from the group consisting of an arylmethyl group, an alkyl group and a hydrogen atom, such as a tetraacylbis(arylmethyl)hexaazaisowurtzitane, a pentaacylarylmethylhexaazaisowurtzitane, a hexaacylhexaazaisowurtzitane, a tetraacyldialkylhexaazaisowurtzitane or a tetraacylhexaazaisowurtzitane (see "Tetrahedron" Vol. 51, No. 16, 4711–4722 (1995), and International Patent Application Publication No. WO 96/23792).

Further, hexaazaisowurtzitane derivatives are known which have an acetyl group, and a formyl group and/or an amino group (NH group) on a hexaazaisowurtzitane skeleton. Examples of such hexaazaisowurtzitane derivatives include a tetraacetyldiformylhexaazaisowurtzitane, a tetraacetylmonoformylmonoaminohexaazaisowurtzitane and a tetraacetyldiaminohexaazaisowurtzitane (International Patent Application Publication No. WO 97/20785).

In these patent and non-patent documents, as a method for isolating an acyl group-containing hexaazaisowurtzitane derivative, use is made of a method in which the reaction solvent is removed from the reaction mixture to obtain the desired compound as a solid, or a method in which the reaction solvent is removed from the reaction mixture to obtain the desired compound as a solid and the solid is then washed with an organic solvent.

However, these isolation methods for an acyl group-containing hexaazaisowurtzitane derivative have a problem in that a satisfactorily high degree of purification cannot be achieved and, hence, it is necessary to purify the isolated acyl group-containing hexaazaisowurtzitane derivative by subjecting it to recrystallization, so that not only does the production cost become high, but also the yield of the desired compound inevitably becomes low.

SUMMARY OF THE INVENTION

In this situation, the present inventors have made extensive and intensive studies with a view toward developing a novel method for producing an acyl group-containing hexaazaisowurtzitane in high purity form in high yield and at low cost. In their studies, they have focused their attention on the fact that various different types of solvents are largely different in the ability to dissolve an acyl group-containing hexaazaisowurtzitane derivative which is the desired compound. As a result of their studies, it has unexpectedly been found that, by using a method which comprises: providing a composition system comprising a mixed solvent of a first solvent and a second solvent respectively having high and low dissolving abilities for the desired compound, wherein the mixed solvent has the desired compound dissolved therein; and (α) removing the first solvent having a high dissolving ability from the composition system to thereby deposit crystals of the desired compound, or (α') causing the above-mentioned composition system to undergo a phase separation into a first solvent phase containing the desired compound dissolved therein and a second solvent phase containing no desired compound or containing only a small amount of the desired compound dissolved therein, followed by removal of the first solvent from the first solvent phase to thereby deposit crystals of the desired compound, the desired compound in high purity form can be obtained in high yield and at low cost. The present invention has been completed, based on these novel findings.

Accordingly, it is an object of the present invention to provide a method for producing an acyl group-containing hexaazaisowurtzitane derivative in high purity form in high yield and at low cost, from a solution of the hexaazaisowurtzitane derivative.

The foregoing and other objects, features and advantages will be apparent to those skilled in the art from the following detailed description and claims.

DETAILED DESCRIPTION OF THE INVENTION

In one aspect of the present invention, there is provided a method for producing an acyl group-containing hexaazaisowurtzitane derivative, which comprises:

(I) providing a composition system comprising:
  (a) a mixed solvent of at least one first solvent selected from the group consisting of water and carboxylic acids and at least one second solvent selected from the group consisting of organic solvents excluding carboxylic acids, and
  (b) an acyl group-containing hexaazaisowurtzitane derivative represented by the following formula (1):

$$WA_nH_{(6-n)} \tag{1}$$

wherein n represents an integer of 4 or 6, each A independently represents an acyl group having 1 to 10 carbon atoms, H represents a hydrogen atom, and W represents a hexavalent hexaazaisowurtzitane residue represented by the following formula (2):

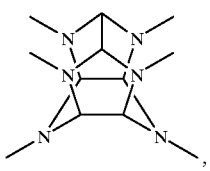
(2)

at least a part of the acyl group-containing hexaazaisowurtzitane derivative (b) being dissolved in the mixed solvent (a);

(II) removing at least a part of the first solvent from the composition system to deposit crystals of the acyl group-containing hexaazaisowurtzitane derivative (b); and (III) isolating the deposited crystals from the composition system.

In another aspect of the present invention, there is provided a method for producing an acyl group-containing hexaazaisowurtzitane derivative, which comprises:

(A) providing a composition system comprising:
(a') a mixed solvent of water and at least one organic solvent which is phase-separable from water, and
(b') an acyl group-containing hexaazaisowurtzitane derivative represented by the following formula (12):

 (12)

wherein n represents an integer of 4 or 6, each A independently represents an acyl group having 1 to 10 carbon atoms, H represents a hydrogen atom, and W represents a hexavalent hexaazaisowurtzitane residue represented by the following formula (13):

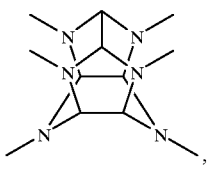
(13)

wherein the composition system comprises an organic phase and an aqueous phase having dissolved therein at least a part of the acyl group-containing hexaazaisowurtzitane derivative (b');

(B) separating the aqueous phase from the composition system; and (C) evaporating the water of the aqueous phase to obtain the hexaazaisowurtzitane derivative (b') in isolated form.

For easy understanding of the present invention, the essential features and various embodiments of the present invention are enumerated below.

1. A method for producing an acyl group-containing hexaazaisowurtzitane derivative, which comprises:

(I) providing a composition system comprising:
(a) a mixed solvent of at least one first solvent selected from the group consisting of water and carboxylic acids and at least one second solvent selected from the group consisting of organic solvents excluding carboxylic acids, and (b) an acyl group-containing hexaazaisowurtzitane derivative represented by the following formula (1):

 (1)

wherein n represents an integer of 4 or 6, each A independently represents an acyl group having 1 to 10 carbon atoms, H represents a hydrogen atom, and W represents a hexavalent hexaazaisowurtzitane residue represented by the following formula (2):

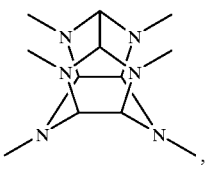
(2)

at least a part of the acyl group-containing hexaazaisowurtzitane derivative (b) being dissolved in the mixed solvent (a);

(II) removing at least a part of the first solvent from the composition system to deposit crystals of the acyl group-containing hexaazaisowurtzitane derivative (b); and (III) isolating the deposited crystals from the composition system.

2. The method according to item 1 above, wherein the acyl group-containing hexaazaisowurtzitane derivative (b) represented by the formula (1) is a product obtained by a synthesis process using at least one reaction solvent.

3. The method according to item 2 above, wherein the at least one reaction solvent is the same as at least one solvent selected from the group consisting of the first solvent and the second solvent, and
wherein, in the composition system provided in step (I), at least one solvent selected from the group consisting of the first solvent and the second solvent is derived from the at least one reaction solvent.

4. The method according to item 1 above, wherein the second solvent has a boiling point which is higher than that of the first solvent, and the removal of at least a part of the first solvent from the composition system is performed by distillation.

5. The method according to item 3 above, wherein the second solvent has a boiling point which is higher than that of the first solvent, and the removal of at least a part of the first solvent from the composition system is performed by distillation.

6. The method according to item 5 above, wherein the acyl group-containing hexaazaisowurtzitane derivative (b) is a tetraacylhexaazaisowurtzitane which is represented by the following formula (3):

 (3)

wherein each of A, H and W is as defined above for the formula (1)
and which is obtained by a synthesis process using at least two reaction solvents,
wherein the at least two reaction solvents are the same as the at least one first solvent and the at least one second solvent, wherein, in the composition system provided in step (I), the at least one first solvent and the at least one second solvent are derived from the at least two reaction solvents, and wherein the at least one first solvent is selected from the group consisting of water and acetic acid and the at least one second solvent is selected from the group consisting of organic solvents having a boiling point which is higher than that of water when the first solvent is water or having a boiling point which is higher than that of acetic acid when the first solvent is acetic acid or a mixture of water and acetic acid.

7. The method according to item 5 above, wherein the acyl group-containing hexaazaisowurtzitane derivative (b) is a tetraacylhexaazaisowurtzitane which is represented by the following formula (3):

$$WA_4H_2 \qquad (3)$$

wherein each of A, H and W is as defined above for the formula (1)
and which is obtained by a synthesis process using at least two reaction solvents, wherein the at least two reaction solvents are the same as the at least one first solvent and the at least one second solvent, wherein, in the composition system provided in step (I), the at least one first solvent and the at least one second solvent are derived from the at least two reaction solvents, and wherein the first solvent is water and the at least one second solvent is selected from the group consisting of amide group-containing organic solvents having a compatibility with water and having a boiling point which is higher than that of water.

8. The method according to item 6 above, wherein the synthesis process for obtaining the tetraacylhexaazaisowurtzitane represented by the formula (3) comprises subjecting a tetraacylbis(arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for the formula (1)
to dearylmethylation in the presence of the at least two reaction solvents.

9. The method according to item 7 above, wherein the synthesis process for obtaining the tetraacylhexaazaisowurtzitane represented by the formula (3) comprises subjecting a tetraacylbis(arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for the formula (1)
to dearylmethylation in the presence of the at least two reaction solvents.

10. The method according to item 5 above, wherein the acyl group-containing hexaazaisowurtzitane derivative (b) is a tetraacylhexaazaisowurtzitane which is represented by the following formula (3):

$$WA_4H_2 \qquad (3)$$

wherein each of A, H and W is as defined above for the formula (1)
and which is obtained by a synthesis process using at least two reaction solvents, wherein the at least two reaction solvents are the same as the at least one first solvent and the at least one second solvent, wherein, in the composition system provided in step (I), the at least one first solvent and the at least one second solvent are derived from the at least two reaction solvents, and wherein the first solvent is water and the at least one second solvent is selected from the group consisting of amide group-containing organic solvents having a compatibility with water and having a boiling point which is higher than that of water, wherein the synthesis process for obtaining the tetraacylhexaazaisowurtzitane represented by the formula (3) comprises the steps of:

(i) subjecting a hexakis(arylmethyl) hexaazaisowurtzitane to reductive dearylmethylation in the presence of an acylating agent to obtain a reaction mixture (i) containing a tetraacylbis (arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for the formula (1) and containing a carboxylic acid and an arylmethane as by-products, (ii) adding water to the reaction mixture, and (iii) subsequently subjecting the resultant to dearylmethylation to thereby produce a reaction mixture (iii) containing a tetraacylhexaazaisowurtzitane of the formula (3), while by-producing an arylmethane.

11. The method according to item 10 above, wherein the carboxylic acid by-produced in step (i) is removed from the reaction mixture (i) obtained in step (i) by azeotropic distillation together with an arylmethane comprising the arylmethane by-product by-produced in step (i).

12. The method according to item 10 above, wherein the carboxylic acid by-produced in step (i) is removed from the composition system, by azeotropic distillation together with an arylmethane comprising the arylmethane by-product by-produced in each of step (i) and step (iii), from the composition system during the removal of the first solvent by distillation in step (II) or from a portion of the composition system which portion remains after the deposited crystals has been isolated from the composition system in step (III).

13. The method according to item 10 above, wherein the second solvent is at least one amide group-containing organic solvent selected from the group consisting of N,N-dimethylacetamide, N,N-dimethylformamide, 1,3-dimethyl-2-imidazolidone and N-methyl-2-pyrrolidone.

14. The method according to item 11 above, wherein the second solvent is at least one amide group-containing organic solvent selected from the group consisting of N,N-dimethylacetamide, N,N-dimethylformamide, 1,3-dimethyl-2-imidazolidone and N-methyl-2-pyrrolidone.

15. The method according to item 12 above, wherein the second solvent is at least one amide group-containing organic solvent selected from the group consisting of N,N-

dimethylacetamide, N,N-dimethylformamide, 1,3-dimethyl-2-imidazolidone and N-methyl-2-pyrrolidone.

16. The method according to item 11 above, wherein the by-produced carboxylic acid is acetic acid and the arylmethane is toluene.

17. The method according to item 12 above, wherein the by-produced carboxylic acid is acetic acid and the arylmethane is toluene.

18. The method according to item 14 above, wherein the by-produced carboxylic acid is acetic acid and the arylmethane is toluene.

19. The method according to item 15 above, wherein the by-produced carboxylic acid is acetic acid and the arylmethane is toluene.

20. The method according to item 4 above, wherein the acyl group-containing hexaazaisowurtzitane derivative (b) is a hexaacylhexaazaisowurtzitane which is represented by the following formula (8):

$$WA_6 \qquad (8)$$

wherein each of W and A is as defined above for the formula (1), and wherein the at least one first solvent is selected from the group consisting of water and acetic acid and the at least one second solvent is selected from the group consisting of ether group-containing organic solvents having a boiling point which is higher than that of water when the first solvent is water or having a boiling point which is higher than that of acetic acid when the first solvent is acetic acid or a mixture of water and acetic acid.

21. The method according to item 5 above, wherein the acyl group-containing hexaazaisowurtzitane derivative (b) is a tetraacyldiformylhexaazaisowurtzitane which is represented by the following formula (9):

$$WA_4F'_2 \qquad (9)$$

wherein each $F'$ represents a formyl group, and each of W and A is as defined above for the formula (1)

and which is obtained by a synthesis process using at least two reaction solvents, wherein the at least two reaction solvents are the same as the at least one first solvent and the at least one second solvent, wherein, in the composition system provided in step (I), the at least one first solvent and the at least one second solvent are derived from the at least two reaction solvents, and wherein the first solvent is formic acid and the at least one second solvent is selected from the group consisting of ether group-containing organic solvents having a boiling point which is higher than that of formic acid.

22. The method according to item 21 above, wherein the synthesis process for obtaining the tetraacyldiformyl-hexaazaisowurtzitane represented by the formula (9) comprises subjecting a tetraacylbis(arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for the formula (1)

to dearylmethylation in the presence of the reaction solvent.

23. The method according to item 21 or 22 above, wherein the synthesis process for obtaining the tetraacyldiformyl-hexaazaisowurtzitane represented by the formula (9) comprises the steps of:

(iii) subjecting a hexakis(arylmethyl)hexaazaisowurtzitane to reductive dearylmethylation in the presence of an acylating agent to obtain a reaction mixture containing a tetraacylbis(arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for the formula (1), (iv) adding formic acid to the reaction mixture, and (v) subsequently subjecting the resultant to dearylmethylation.

24. The method according to item 21 above, wherein the second solvent is at least one ether group-containing organic solvent selected from the group consisting of ethylene glycol diethyl ether, ethylene glycol di-n-butyl ether, diethylene glycol dimethyl ether and diethylene glycol diethyl ether.

25. The method according to item 22 above, wherein the second solvent is at least one ether group-containing organic solvent selected from the group consisting of ethylene glycol diethyl ether, ethylene glycol di-n-butyl ether, diethylene glycol dimethyl ether and diethylene glycol diethyl ether.

26. The method according to item 23 above, wherein the second solvent is at least one ether group-containing organic solvent selected from the group consisting of ethylene glycol diethyl ether, ethylene glycol di-n-butyl ether, diethylene glycol dimethyl ether and diethylene glycol diethyl ether.

27. A method for producing an acyl group-containing hexaazaisowurtzitane derivative, which comprises:

(A) providing a composition system comprising:

(a') a mixed solvent of water and at least one organic solvent which is phase-separable from water, and (b') an acyl group-containing hexaazaisowurtzitane derivative represented by the following formula (12):

$$WA_nH_{(6-n)} \qquad (12)$$

wherein n represents an integer of 4 or 6, each A independently represents an acyl group having 1 to 10 carbon atoms, H represents a hydrogen atom, and W represents a hexavalent hexaazaisowurtzitane residue represented by the following formula (13):

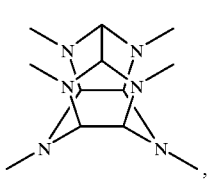

(13)

wherein the composition system comprises an organic phase and an aqueous phase having dissolved therein at least a part of the acyl group-containing hexaazaisowurtzitane derivative (b');

(B) separating the aqueous phase from the composition system; and (C) evaporating the water of the aqueous phase to obtain the hexaazaisowurtzitane derivative (b') in isolated form.

28. The method according to item 27 above, wherein n in the formula (12) is 4.

29. The method according to item 27 above, wherein n in the formula (12) is 6, and wherein two A groups in the formula (12) are formyl groups and the remaining four A groups are acyl groups excluding a formyl group.

As mentioned above, the method according to one aspect (first aspect) of the present invention comprises the above-mentioned steps (I) to (III), and the method according to another aspect (second aspect) of the present invention comprises the above-mentioned steps (A) to (C).

1. The method of the first aspect:

In step (I) of the method of the first aspect of the present invention, there is provided a composition system comprising:

(a) a mixed solvent of at least one first solvent selected from the group consisting of water and carboxylic acids and at least one second solvent selected from the group consisting of organic solvents excluding carboxylic acids, and (b) an acyl group-containing hexaazaisowurtzitane derivative represented by the following formula (1):

(1)

wherein n represents an integer of 4 or 6, each A independently represents an acyl group having 1 to 10 carbon atoms, H represents a hydrogen atom, and W represents a hexavalent hexaazaisowurtzitane residue represented by the following formula (2):

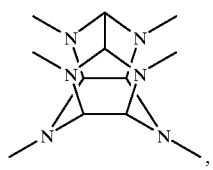

(2)

at least a part of the acyl group-containing hexaazaisowurtzitane derivative (b) being dissolved in the mixed solvent (a).

In step (II) of the method of the first aspect, at least a part of the first solvent is removed from the composition system to deposit crystals of the acyl group-containing hexaazaisowurtzitane derivative (b).

In step (III) of the method of the first aspect, the deposited crystals are isolated from the composition system.

The method of the first aspect of the present invention takes advantage of the fact that the acyl group-containing hexaazaisowurtzitane derivative represented by the formula (1) is almost insoluble in an ordinary organic solvent, but can be easily dissolved in a protonic highly polar solvent, such as water and carboxylic acids, differing from hexaazaisowurtzitane derivatives other than the hexaazaisowurtzitane derivative of the formula (1) and skeletal decomposition products of the hexaazaisowurtzitane skeleton, wherein these other hexaazaisowurtzitane derivatives and skeletal decomposition products are contained in the composition system as impurities. Utilizing this property of the hexaazaisowurtzitane derivative of the formula (1), in the method of the first aspect, the acyl group-containing hexaazaisowurtzitane derivative of the formula (1) is dissolved in a mixed solvent of a first solvent and a second solvent to thereby form a composition system, wherein the first solvent (i.e., water or a carboxylic acid) has the ability to dissolve the acyl group-containing hexaazaisowurtzitane derivative of the formula (1), and the second solvent (i.e., an organic solvent excluding carboxylic acids) has almost no ability to dissolve the acyl group-containing hexaazaisowurtzitane derivative of the formula (1) but has the ability to dissolve the above-mentioned impurities, and subsequently at least a part of the first solvent is removed from the composition system to deposit crystals of the acyl group-containing hexaazaisowurtzitane derivative, and the deposited crystals are isolated from the composition system. Thus, a high purity hexaazaisowurtzitane derivative of the formula (1) can be obtained.

Examples of acyl group-containing hexaazaisowurtzitane derivatives of the formula (1) include the compounds which respectively have the structures represented by the following formulae (1-1) to (1-3):

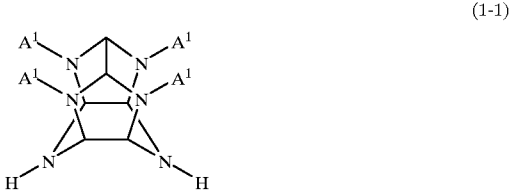

(1-1)

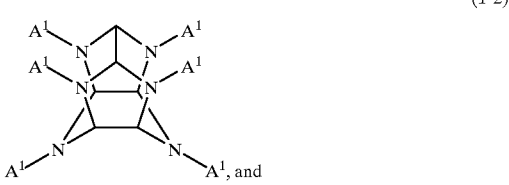

(1-2)

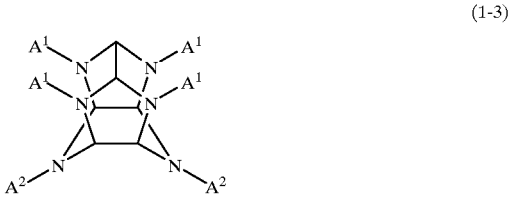

(1-3)

wherein each $A^1$ independently represents an acyl group having 1 to 10 carbon atoms, each $A^2$ independently represents an acyl group having 1 to 10 carbon atoms, and H represents a hydrogen atom, wherein $A^1$ and $A^2$ are different from each other.

With respect to acyl group A in the formula (1), there is no particular limitation as long as it is an acyl group having 1 to 10 carbon atoms. Specific examples of acyl groups A include a formyl group, an acetyl group, a propionyl group, a butyryl group, an isobutyryl group, a valeryl group, a hexanoyl group and a 2-phenylacetyl group. Of these, acyl groups having 1 to 3 carbon atoms, such as a formyl group, an acetyl group and a propionyl group, are preferred, and a formyl group and an acetyl group are especially preferred.

The above-mentioned first solvent is at least one solvent selected from the group consisting of water and carboxylic acids. With respect to the carboxylic acids, there is no particular limitation as long as they are liquid under atmospheric pressure and at a temperature of 40° C. or more. Examples of carboxylic acids include straight chain carboxylic acids, such as formic acid, acetic acid, propionic acid, butyric acid, and isobutyric acid. With respect to the carboxylic acids, when it is intended to remove the first solvent by distillation, low molecular weight carboxylic acids, such as formic acid, acetic acid and propionic acid, are preferred because each of these low molecular weight carboxylic acids has a low boiling point. Of these low molecular weight carboxylic acids, formic acid and acetic acid are especially preferred.

With respect to the above-mentioned second solvent, there is no particular limitation as long as it is an organic solvent other than carboxylic acids. However, it is preferred to use as the second solvent an organic solvent in which the acyl group-containing hexaazaisowurtzitane derivative exhibits a solubility of 1% by weight or less, more preferably 0.5% by weight or less.

With respect to the hexaazaisowurtzitane derivative (b) of the formula (1) contained in the above-mentioned composition system which is subjected to the crystal deposition process of step (II), it is preferred to use a product obtained by a synthesis process using at least one reaction solvent. In this case, it is more preferred that the above-mentioned at least one reaction solvent used in the synthesis process is the same as at least one solvent selected from the group consisting of the first solvent and the second solvent. The reason for this resides in that, since the reaction solvent (used in the synthesis process) as such is used in the mixed solvent (a) contained in the above-mentioned composition system, the production process becomes simple.

With respect to the above-mentioned composition system, the hexaazaisowurtzitane derivative (b) of the formula (1) need not be completely dissolved in the mixed solvent (a) and the hexaazaisowurtzitane derivative (b) may be present in the composition system in the form of a slurry, in which a part of the hexaazaisowurtzitane derivative (b) is not dissolved in the mixed solvent (a). However, it is preferred that the composition system contains no solids.

In the above-mentioned crystal deposition step [step (II)] of the method of the present invention, it is required that at least a part of the first solvent (at least one solvent selected from the group consisting of water and carboxylic acids) is removed from the composition system to deposit crystals of the hexaazaisowurtzitane derivative (b). With respect to the method for conducting the deposition of crystals, there is no particular limitation. However, as specific examples of such a method, there can be mentioned the following four methods:

A. (Distillative crystal deposition method)

Distillative crystal deposition method can be employed when the second solvent has a boiling point which is higher than that of the first solvent. In this method, the composition system is subjected to distillation to thereby remove at least a part of the first solvent to deposit crystals of the hexaazaisowurtzitane derivative (b).

B. (Membrane filtration separation method)

Membrane filtration separation method comprises subjecting the composition system to filtration by using a filter membrane to thereby selectively remove the first solvent and deposit crystals of the hexaazaisowurtzitane derivative (b).

C. (Adsorption method)

Adsorption method is a method in which the removal of the first solvent is conducted by using an adsorber which is capable of selectively adsorbing the first solvent, to thereby deposit crystals of the hexaazaisowurtzitane derivative (b).

D. (Chemical reaction method)

Chemical reaction method comprises converting the first solvent to other compounds by a chemical reaction to thereby deposit crystals of the hexaazaisowurtzitane derivative (b).

In any one of the above methods, almost all of the impurities are caused to be dissolved in the second solvent so that the resultant deposited crystals of the hexaazaisowurtzitane derivative (b) contain only a very small amount of impurities.

Of the above-mentioned four methods, the distillative crystal deposition method is preferred because this method is most suitable for obtaining an acyl group-containing hexaazaisowurtzitane derivative in especially high purity form.

Hereinbelow, detailed explanation is made with respect to the distillative crystal deposition (method A).

In the present invention, when it is intended to conduct the crystal deposition process of step (II) by the distillative crystal deposition method, there is no particular limitation with respect to the combination of the first solvent and the second solvent as long as the second solvent has a boiling point which is higher than that of the first solvent.

Examples of first solvents include water (boiling point: 100° C.), formic acid (boiling point: 100 to 101° C.), acetic acid (boiling point: 118° C.), propionic acid (boiling point: 141° C.). Examples of second solvents include amide group-containing organic solvents, such N,N-dimethylformamide (boiling point: 153° C.), N,N-dimethylacetamide (boiling point: 165 to 166° C.), 1,3-dimethyl-2-imidazolidone (boiling point: 220° C./754 mmHg) and N-methyl-2-pyrolidone (boiling point: 202° C.); and ether group-containing organic solvents, such as ethylene glycol diethyl ether (boiling point: 121° C.), ethylene glycol di-n-butyl ether (boiling point: 203° C.), diethylene glycol dimethyl ether (boiling point: 162° C.), diethylene glycol diethyl ether (boiling point: 188° C.) and diethylene glycol dibutyl ether (boiling point: 256° C.).

In this connection, it should be noted that, when an organic solvent having a boiling point which is the same as or higher than that of propionic acid is used as the first solvent, a solvent which has a boiling point which is lower than that of propionic acid, such as ethylene glycol diethyl ether, cannot be used as the second solvent.

The above-mentioned second solvents are polar solvents having particularly high compatibility with the above-mentioned first solvents and, therefore, can be used to obtain a uniform mixture of the first solvent and the second solvent. However, in the present invention, the mixed solvent (a) need not be a uniform mixture of the first solvent and the second solvent, and the mixed solvent (a) may be a two-phase mixture comprising the first solvent and the second solvent. Even when the mixed solvent (a) is a two-phase mixture, the distillative deposition method can be employed as long as the above-mentioned relationship between the boiling point of the first solvent and the boiling point of the second solvent is satisfied. With respect to the weight ratio of the first solvent to the second solvent in the mixed solvent (a), the weight ratio is generally from 0.01 to 10, preferably from 0.02 to 5, more preferably from 0.05 to 2.

With respect to the distillation pressure, either the atmospheric pressure or the reduced pressure may be employed. With respect to the distillation temperature, there is no particular limitation as long as the first solvent can be distilled under the pressure conditions employed for the distillation. However, for completing the distillation within a short period of time, it is preferred to perform the distillation under reduced pressure and at a temperature which is equal to or higher than the boiling point of the first solvent as measured under the reduced pressure employed. It is more preferred to perform the distillation under reduced pressure and at a temperature which is equal to or higher than the boiling point of the first solvent and which is equal to or lower than the boiling point of the second solvent, wherein each of the boiling points of the first and second solvents is as measured under the reduced pressure employed. When the distillation is conducted under such pressure and temperature conditions, it becomes possible to separate the first solvent from the composition system in a single distillation process, so that each of the first solvent and the second solvent can be easily recycled. When the distillation is conducted under reduced pressure, the pressure is selected within the range of from 0.0000001 mmHg to 760 mmHg. In this case, the smaller the pressure, the less the time required for the distillation and the lower the temperature required for carrying out the distillation, so that it becomes advantageously possible to suppress the occurrence of the thermal decomposition of the an acyl group-containing hexaazaisowurtzitane derivative (b) of the formula (1). It is preferred to perform the distillation under a reduced pressure of 200 mmHg or less.

In the present invention, when the distillative crystal deposition method is employed, and some of the second solvent may also be distilled when the first solvent is removed by distillation, as long as about 10% by weight or more of the second solvent present in the original composition system is left unremoved. Further, complete removal of the first solvent from the composition system is not necessary. In fact, depending on the type of the first solvent and the type of the second solvent, it is very difficult to completely remove the first solvent from the composition system in a commercial scale practice of the distillation. Therefore, in the distillative crystal deposition method, distillation may be conducted until the amount of the first solvent remaining in the resultant distillation residue becomes 0.2 or less in terms of the weight ratio of the first solvent remaining in the composition system to the second solvent. For obtaining the desired compound in high yield, it is preferred to conduct the distillation until the amount of the first solvent remaining in the composition system becomes 0.02 or less in terms of the weight ratio of the first solvent to the second solvent.

In the method of the first aspect of the present invention, when the distillative crystal deposition method is employed, it is especially preferred that the compound subjected to the crystal deposition process is a tetraacylhexaazaisowurtzitane represented by the following formula (3), which is a compound of the formula (1) in which n is 4:

$$WA_4H_2 \quad (3)$$

wherein each of A, H and W is as defined above for the formula (1).

The tetraacylhexaazaisowurtzitane of the formula (3) is advantageous in that this compound is highly hydrophilic, so that it exhibits low solubility in almost all organic solvents exclusive of carboxylic acids.

Examples of first solvents which can be used in the composition system in order to deposit crystals of the tetraacylhexaazaisowurtzitane include water, acetic acid and propionic acid. Of these, water and acetic acid are preferred, and water is more preferred. With respect to the second solvent, there is no particular limitation as long as it is an organic solvent exclusive of carboxylic acids. However, it is preferred to use organic solvents in which the tetraacyl-hexaazaisowurtzitane represented by the formula (3) above exhibits a solubility of 0.5% by weight or less. Preferred examples of such second solvents include an amide group-containing solvent and an ether group-containing solvent. Of these, an amide group containing solvent is more preferred, because it can be advantageously used for obtaining an acyl group-containing hexaazaisowurtzitane in especially high purity form. Specifically, N,N-dimethylacetamide, N,N-dimethylformamide, and N-methyl-2-pyrrolidone are preferred, and N,N-dimethylacetamide is more preferred.

With respect to the tetraacylhexaazaisowurtzitane of the formula (3) subjected to crystal deposition process, there is no particular limitation with respect to the method for the synthesis thereof. However, it is preferred to use a tetraacylhexaazaisowurtzitane synthesized by subjecting a tetraacylbis(arylmethyl)hexaazaisowurtzitane represented by the following formula (4) to dearylmethylation as schematically shown in the following reaction formula (5):

$$WA_4B_2 \quad (4)$$

$$WA_4B_2 \xrightarrow{\text{dearylmethylation}} WA_4H_2 \quad (5)$$

wherein each B independently represents an arylmethyl group having 7 to 21 carbon atoms, and each of W, A and H is defined above for the formula (1).

With respect to the reaction represented by the reaction formula (5), any reaction method can be used as long as it can perform a dearylmethylation reaction. Examples of reaction methods include a reductive dearylmethylation method; an oxidation dearylmethylation method using an oxidizing agent, such as peroxide, ruthenium oxide or $(NH_4)[Ce(IV)(NO_3)_6]$; a reaction method in which, after effecting carbamation using chloroformate, a decarboxylation is conducted to thereby form N—H groups. Of these, the reductive dearylmethylation method is especially preferred from the viewpoint of high selectivity.

With respect to a reaction solvent to be used in the dearylmethylation reaction represented by the reaction formula (5), there is no particular limitation as long as the solvent is capable of dissolving a tetraacylbis(arylmethyl)hexaazaisowurtzitane of the formula (4) and the solvent does not adversely affect the reaction. Examples of reaction solvents include amide group-containing solvents, such as N,N-dimethylacetamide, N,N-dimethylformamide, 1,3-dimethyl-2-imidazolidone and N-methyl-2-pyrrolidone; and carboxylic acids, such as acetic acid and propionic acid. These solvents have a relatively high ability to dissolve a tetraacylbis-(arylmethyl)hexaazaisowurtzitane, so that, when these solvents are used as a first component reaction solvent, any other solvents can be used as a second component reaction solvent, wherein the first and second component reaction solvents constitute a whole reaction solvent system.

Below described are solvents which can be advantageously used as the second component reaction solvent when an amide group-containing solvent or a carboxylic acid is used as the first component reaction solvent.

When an amide group-containing solvent is used as the first component reaction solvent, it is preferred that, as the second component reaction solvent, use is made of water or a carboxylic acid, such as acetic acid, propionic acid or the like, which is capable of dissolving a tetraacylhexaazaisowurtzitane of the formula (3). The reason for this resides not only in that, when water or a carboxylic acid is used as the second component reaction solvent, the reaction can be conducted in a homogeneous reaction system, but also in that the water or carboxylic acid and the amide group-containing solvent can, respectively, serve as the first solvent and the second solvent in the composition system to be subjected to a distillative crystal deposition by removing the first solvent, so that an obtained reaction mixture containing the tetraacylhexaazaisowurtzitane of the formula (3) can be used as such in the distillative crystal deposition without a need for removal of the reaction solvent. The type of the carboxylic acid as the second component reaction solvent is not particularly limited. A plurality of types of carboxylic acids can be used individually or in combination. As the second component reaction solvent, water is particularly preferred, since water has a lower boiling point than that of a carboxylic acid.

Carboxylic acids are capable of dissolving both a tetraacylbis(arylmethyl)hexaazaisowurtzitane and a tetraacylhexaazaisowurtzitane. Therefore, when a carboxylic acid is used as the first component reaction solvent, even if any organic solvent, without any limitation, is used as the second component reaction solvent, the reaction proceeds in a homogeneous system. A carboxylic acid used as the first component reaction solvent also functions as the first solvent in the composition system to be subjected to distillative crystal deposition. Therefore, when an organic solvent, which has a boiling point higher than that of a carboxylic acid used as the first component reaction solvent and which, hence, can serve as the second solvent in the composition system to be subjected to distillative crystal deposition, is used as the second component reaction solvent, an obtained reaction mixture containing the tetraacylhexaazaisowurtzitane of the formula (3), as such, can be used as the composition system to be subjected to distillative crystal deposition. The addition of the second component reaction solvent may be made after completion of the reaction for the synthesis of the tetraacylhexaazaisowurtzitane of the formula (3) and just before subjecting the resultant synthesis reaction mixture to distillative crystal deposition.

When a carboxylic acid is used as the first component reaction solvent, there is no particular limitation with respect to the second component reaction solvent. However, preferred are organic solvents in which the tetraacylhexaazaisowurtzitane of the formula (3) exhibits a solubility of 0.5% by weight or less and which has a boiling point which is higher than that of the carboxylic acid. Examples of such preferred solvents include ether group-containing solvents, such as ethylene glycol diethyl ether, ethylene glycol di-n-butyl ether, diethylene glycol dimethyl ether, diethylene glycol diethyl ether, diethylene glycol dibutyl ether and the like, and amide group-containing solvents, such as N,N-dimethylacetamide, N,N-dimethylformamide, 1,3-dimethyl-2-imidazolidone, N-methyl-2-pyrrolidone and the like. The above-mentioned solvents can be used individually or in combination.

The amount of the tetraacylbis(arylmethyl)hexaazaisowurtzitane used in the reaction of the formula (5) is generally in the range of from 0.001 to 1, preferably from 0.005 to 0.5, more preferably from 0.01 to 0.4, in terms of the weight ratio thereof to the reaction solvent.

As a reducing agent optionally used for the dearylmethylation reaction, hydrogen gas, hydrazine or the like can be mentioned, and hydrogen gas is preferred.

The reducing agent is used generally in an amount of from 1 to 10000, preferably from 1 to 1000, more preferably from 2 to 50, in terms of the molar ratio of the reducing agent to the arylmethyl groups of the tetraacylbis(arylmethyl) hexaazaisowurtzitane. When hydrogen gas is used as a reducing agent, the reaction pressure is generally in the range of from 0.01 to 100, preferably from 0.1 to 30, more preferably from 0.1 to 20 kgf/cm², in terms of the hydrogen partial pressure. In addition to the hydrogen gas, inert gases, such as nitrogen, argon and helium gases may be present in the reaction system.

With respect to the reduction catalyst, which is optionally employable, there is no particular limitation as long as it is capable of advancing the dearylmethylation of tetraacylbis (arylmethyl)hexaazaisowurtzitane. As the reduction catalyst, a catalyst containing a metal belonging to the platinum family or containing a derivative thereof, is generally used. Preferred examples of reduction catalysts include Pd compounds [such as $Pd(OAc)_2$, $PdCl_2$, $Pd(NO_3)_2$, PdO, $Pd(OH)_2$, $Pd_3Pb_1$ and $Pd_3Te_1$], Pd alloys and metallic Pd; and Ru compounds (such as $RuCl_3$), Ru alloys and metallic Ru. Of these, Pd compounds [such as $Pd(OAc)_2$, $PdCl_2$ and the like], Pd alloys and metallic Pd are more preferred. These reduction catalysts as such can be used. Alternatively, these reduction catalysts can be used in such a form as carried on various types of carriers, such as activated carbon, silica, alumina, silica-alumina, zeolite, activated clay, zirconia and titania. For improving the catalyst activity, it is preferred that the catalyst is subjected to reduction treatment prior to use in the above-mentioned reductive dearylmethylation reaction. As the reducing agent for performing this reduction treatment, hydrogen gas or hydrazine is preferred. When the use of a catalyst carried on a carrier is intended, the surface of the carrier may be treated so as to inactivate acid sites present on the surface of the carrier by silylation, acylation or the like, or so as to adsorb an alkaline substance (e.g., NaOH) on the surface of the carrier, or so as to effect an activation of the carrier to thereby increase acid sites on the surface of the carrier.

When a heterogenous reduction catalyst is used, it can be used in the form of either a fixed bed or a fluidized bed.

The reaction temperature for the reductive dearylmethylation is generally in the range of from the coagulation temperature of the solvent to 200° C., preferably from 30 to 180° C., more preferably from 40 to 165° C.

With respect to the method for obtaining the tetraacylhexaazaisowurtzitane of the formula (3) to be subjected to distillative crystal deposition in the method of the present invention, it is preferred to use a two-step reaction method comprising a first step in which a hexakis(arylmethyl) hexaazaisowurtzitane is subjected to reductive dearylmethylation in the presence of an acylating agent to obtain a tetraacylbis(arylmethyl)hexaazaisowurtzitane [as shown by the following reaction formula (6)], and a second step in which the obtained tetraacylbis(arylmethyl) hexaazaisowurtzitane is subjected to dearylmethylation to obtain a tetraacylhexaazaisowurtzitane [as shown by the above reaction formula (5)].

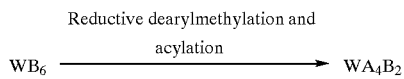

(6)

wherein B represents an arylmethyl group having 7 to 21 carbon atoms, and each of W and A is as defined above for the formula (1).

With respect to a reaction solvent used in the reductive dearylmethylation [represented by the above reaction formula (6)] which is performed in the presence of an acylating agent, there is no particular limitation as long as the solvent is capable of dissolving solving the $WB_6$ and the solvent does not adversely affect the reaction. Examples of solvents include amide group-containing solvents, such as N,N-dimethylacetamide, N,N-dimethylformamide, 1,3-dimethyl-2-imidazolidone and N-methyl-2-pyrrolidone, and ether group-containing solvents, such as ethylene glycol diethyl ether, ethylene glycol di-n-butyl ether, diethylene glycol dimethyl ether, diethylene glycol diethyl ether and diethylene glycol dibutyl ether. Among these solvents, N,N-dimethylacetamide and N,N-dimethylformamide are preferred. The above-mentioned solvents can be used individually or in combination.

The solvents mentioned above as being useful for the reaction of the reaction formula (6) have advantages in that they can also be used as a second solvent in the composition system to be subjected to distillative crystal deposition. Therefore, when a tetraacylbis(arylmethyl)hexaazaisowurtzitane is produced by the reaction of the above reaction formula (6) by using the above-mentioned solvents (usable as a second solvent), it is not necessary to isolate the produced tetraacylbis(arylmethyl)hexaazaisowurtzitane from a reaction mixture obtained by the reaction of the reaction formula (6). The subsequent operations can be easily performed by a method in which a solvent usable as a first solvent in the composition system to be subjected to distillative crystal deposition is added to the reaction mixture obtained by the reaction of the reaction formula (6), and the resultant mixture containing the tetraacylbis(arylmethyl)hexaazaisowurtzitane and the first and second solvents is subjected to dearylmethylation or both dearylmethylation and acylation to obtain a reaction mixture (composition system) containing the desired tetraacylhexaazaisowurtzitane of the formula (3), and the obtained composition system is subjected to distillative crystal deposition by removing at least a part of the first solvent from the composition system to deposit crystals of the desired compound, and the deposited crystals are isolated from the composition system.

The amount of $WB_6$ used in the reaction of the reaction formula (6) is generally in the range of from 0.001 to 1, preferably from 0.005 to 0.5, more preferably from 0.01 to 0.4, in terms of the weight ratio of the $WB_6$ to the reaction solvent.

As a reducing agent used in reductive dearylmethylation and acylation [as represented by the above reaction formula (6)] which is performed in the presence of an acylating agent, hydrogen gas or formic acid can be mentioned. Hydrogen gas is preferred.

The amount of the reducing agent is generally in the range of from 0.1 to 10000, preferably from 0.67 to 1000, more preferably from 2 to 50, in terms of the molar ratio of the reducing agent to the arylmethyl groups contained in the $WB_6$. When hydrogen gas is used as a reducing agent, the reaction pressure is generally in the range of from 0.01 to 100, preferably from 0.1 to 30, more preferably from 0.1 to 15 kgf/cm$^2$, in terms of hydrogen partial pressure. In addition to the hydrogen gas, inert gases, such as nitrogen, argon and helium gases, may be present in the reaction system.

With respect to the reduction catalyst for the reductive dearylmethylation in the presence of an acylating agent in the process of the formula (6) above, there is no particular limitation as long as it can advance the reductive dearylmethylation reaction of the $WB_6$. The reduction catalysts and reduction conditions which are mentioned in connection with the dearylmethylation of the above-mentioned tetraacylbis(arylmethyl)hexaazaisowurtzitane can be employed.

With respect to the acylating agent used in the process of the formula (6) for the reductive dearylmethylation accompanied by acylation, there is no particular limitation as long as it is capable of acylating a secondary amino group to form an N-acyl bond. Examples of acylating agents include carboxylic anhydrides, such as acetic anhydride, propionic anhydride, formic anhydride, lactic anhydride and an anhydride of a mixture of acetic acid and formic acid; carboxylic esters of N-hydroxysuccinimide, such as N-acetoxysuccinimide, N-propionyloxysuccinimide and N-(2-phenylacetoxy)succinimide; and acylimidazoles, such as acetylimidazole and propionylimidazole. Among these acylating agents, carboxylic anhydrides, such as acetic anhydride, propionic anhydride and an anhydride of a mixture of acetic acid and formic acid are preferred, and acetic anhydride is more preferred.

The amount of the acylating agent varies depending on the reactivity of the acylating agent, the reaction mode and the reaction conditions. The acylating agent is used generally in an amount of from 0.67 to 100, preferably from 0.67 to 10, more preferably from 0.67 to 3, in terms of the molar ratio of the acylating agent to the arylmethyl groups of the $WB_6$.

The reaction temperature for the reductive dearylmethylation in the presence of an acylating agent in the process of the formula (6) above is generally within the range of from the coagulation temperature of the reaction solvent to 200° C., preferably from 30 to 180° C., more preferably from 40 to 165° C. For suppressing the skeletal decomposition of the $WB_6$ which is likely to occur when the $WB_6$ is in the solvent for a long period of reaction time, it is preferred that the process of the formula (6) is conducted at a relatively low temperature, namely 40 to 80° C. However, the reaction may also be conducted at a relatively high temperature, namely 100 to 200° C., since, at 100 to 200° C., not only can the solubility of $WB_6$ be increased, thereby enabling the reaction to be performed at a high concentration of $WB_6$, but also the produced $WA_4B_2$ can remain dissolved in the reaction solvent and hence can be easily separated from a solid catalyst.

When an amide group-containing organic solvent is employed in the reductive dearylmethylation (which is conducted in the presence of an acylating agent) in the process of the formula (6), there is an advantage in that the skeletal decomposition of $WB_6$ can be suppressed even when the reaction is conducted at a temperature of from 20 to 165° C. This effect of an amide group-containing organic solvent, which is the suppression of the skeletal decomposition of $WB_6$, is exerted by the weak basicity of the solvent. The reason for this effect is as follows. In the reductive dearylmethylation which is conducted in the presence of an acylating agent, acidic protons are formed due to the acylation of the secondary amine by the acylating agent, and the formed acidic protons cause the skeletal decomposition of the $WB_6$. However, by using a weakly basic, amide group-containing organic solvent as a reaction solvent, the acidic protons are neutralized, thereby maintaining the acidity of the reaction system at a low level, so that the skeletal decomposition of $WB_6$ can be suppressed even when the reaction is conducted at high temperatures.

As apparent from the above, with respect to the reductive dearylmethylation (which is conducted in the presence of an acylating agent) in the process of the formula (6), the use of an amide group-containing organic solvent as a reaction solvent is especially preferred because the suppression of the skeletal decomposition of $WB_6$ leads to an increase in the reaction yield.

The same effect as achieved by using an amide group-containing solvent (which has a weak basicity) can also be obtained by using ether group-containing solvents, such as ethylene glycol diethyl ether, ethylene glycol di-n-butyl ether, diethylene glycol dimethyl ether, diethylene glycol diethyl ether and diethylene glycol dibutyl ether.

With respect to the method for performing the reductive dearylmethylation (which is conducted in the presence of an acylating agent) in the process of the formula (6), there can be employed a method in which $WB_6$, an acylating agent, a reaction solvent, a reduction catalyst and a reducing agent are placed in a reaction vessel and stirred at a predetermined temperature. Preferred is a reaction method in which a reduction catalyst and a reducing agent are first placed in a reaction vessel and kept at a predetermined temperature, and then a solution obtained by dissolving $WB_6$ in a reaction solvent is added to the reaction vessel together with an acylating agent. Also preferred is a reaction method in which a reduction catalyst and a reducing agent are first placed in a reaction vessel and kept at a predetermined temperature, and then a solution obtained by dissolving $WB_6$ and an acylating agent in a reaction solvent is added to the reaction vessel.

When the desired compound contained in the composition system to be subjected to distillative crystal deposition is the tetraacylhexaazaisowurtzitane of the formula (3), it is especially preferred that the reaction solvent used for the reductive dearylmethylation (which is conducted in the presence of an acylating agent) in the process of the formula (6) is an amide group-containing solvent. The reason for this is as follows. An amide group-containing solvent has the high ability to dissolve a tetraacylbis(arylmethyl) hexaazaisowurtzitane. Therefore, when an amide group-containing solvent is used as the reaction solvent in the reductive dearylmethylation (which is conducted in the presence of an acylating agent) in the process of the formula (6), the produced tetraacylbis(arylmethyl) hexaazaisowurtzitane can remain dissolved in an obtained reaction mixture. After completion of the reaction of the process of the formula (6), water (which will serve as a first solvent in the distillative crystal deposition) is added to the reaction mixture, and the resultant mixture is subjected to dearylmethylation of the formula (5), to thereby obtain a reaction mixture containing the desired tetraacylhexaazaisowurtzitane which is dissolved in the water. Thus, the reactions of the formulae (6) and (5) can be consecutively smoothly performed by allowing all hexaazaisowurtzitane compounds [namely, hexakis(arylmethyl) hexaazaisowurtzitane, tetraacylbis(arylmethyl) hexaazaisowurtzitane and tetraacylhexaazaisowurtzitane] to remain dissolved in a reaction solvent. Further, since the reaction mixture obtained by the dearylmethylation of the formula (5) already contains first and second solvents, the reaction mixture as such can be used as a composition system to be subjected to the distillative crystal deposition.

When the dearylmethylation reactions of the formulae (6) and (5) are consecutively performed [that is, when the production of tetraacylbis(arylmethyl)hexaazaisowurtzitane and the subsequent production of tetraacylhexaazaisowurtzitane therefrom are consecutively performed to obtain a composition system which can be consecutively subjected to the distillative crystal deposition], it is preferred that the acylating agent to be used in the reductive dearylmethylation of the formula (6) is a carboxylic anhydride, more preferably acetic anhydride.

In the acylating reaction (using a carboxylic anhydride) according to the formula (6), a carboxylic acid, which has a boiling point which is higher than that of water, is by-produced. When it is intended to recycle and reuse the reaction solvent used, it is necessary to remove the by-produced carboxylic acid. For removal of the by-produced carboxylic acid, it is preferred to use a method in which the by-produced carboxylic acid is removed by azeotropic distillation together with an arylmethane, such as toluene or xylene.

With respect to the above-mentioned arylmethane used for the above-mentioned azeotropic distillation, it is preferred to utilize:
  an arylmethane by-produced during the reductive dearylmethylation of the reaction formula (6); or
  a mixture of an arylmethane by-produced during the reductive dearylmethylation of the reaction formula (6), and an arylmethane by-produced in the dearylmethylation of the reaction formula (5).

Further, it is also preferred that an additional arylmethane is added to the reaction system of the reaction of the reaction formula (6) and/or the reaction mixture obtained by the reaction of the reaction formula (6). With respect to a timing for conducting the azeotropic distillation and to a method for conducting the azeotropic distillation, there is no particular limitation. However, it is preferred that the azeotropic distillation is conducted by a method wherein the by-produced carboxylic acid and the by-produced arylmethane and/or the additional arylmethane are removed together by azeotropic distillation from: (x) the reaction mixture obtained after completion of the reductive dearylmethylation of the formula (6); (y) the composition system during the removal of the first solvent by distillation in step (II); or (z) a portion of the composition system which portion remains after the deposited crystals have been isolated from the composition system in step (III). Specifically, for example, in the case where the above-mentioned reaction mixture as mentioned in (x) above is subjected to azeotropic distillation, when it is intended to use water as the first solvent, it is preferred to use as compound (b) a tetraacylhexaazaisowurtzitane produced by a method comprising performing the reductive dearylmethylation of the reaction formula (6) in the presence of an acylating agent using as a solvent an amide-group containing organic solvent; performing the dearylmethylation of the reaction formula (5) using as a solvent an amide-group containing organic solvent; and conducting the azeotropic distillation, wherein the azeotropic distillation is conducted after completion of the reaction of the reaction formula (5) and before addition of water to the reaction system, so as to prevent the carboxylic acid by-produced during the reaction of the reaction formula (6) from causing the hydrolysis of the amide group-containing organic solvent. Further, in the cases where the composition system as mentioned in (y) above and where the portion of the composition system as mentioned in (z) above is subjected to azeoptropic distillation, the azeotropic distillations can be advantageously conducted by utilizing the arylmethane by-produced during the reaction of the reaction formula (6) and by utilizing the arylmethan by-produced during the reactions of the reaction formulae (6) and (5), respectively. As another example of preferred methods of the present invention in which the azeotropic distillation is conducted, there can be mentioned a method wherein water is used as the first solvent, and wherein (1) the distillative crystal deposition is conducted under a reduced pressure of 200 mmHg or less (i.e., the distillative crystal deposition method) so that the distillation can be conducted at a low temperature to thereby suppress the occurrence of the hydrolysis of the amide group-containing organic solvent, and (2) by the azeotropic distillation (that is, the azeotropic distillation is conducted after the removal of water by distillation) is conducted. With respect to the arylmethane used in the azeotropic distillation, it is preferred to use toluene.

As another preferred example of the tetraacylhexaazaisowurtzitanes of the formula (3), there can be mentioned a tetraacylhexaazaisowurtzitane which is obtained by the synthesis process using at least one reaction solvent which is the same as at least one solvent selected from the group consisting of the first solvent and the second solvent, wherein the synthesis process for obtaining the tetraacylhexaazaisowurtzitane comprises subjecting a hexakis(arylmethyl) hexaazaisowurtzitane to the reductive dearylmethylation represented by the following reaction formula (7) in the presence of an acylating agent, to thereby obtain a reaction mixture containing the tetraacylhexaazaisowurtzitane and the at least one reaction solvent;

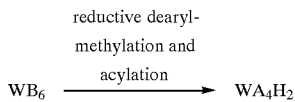

(7)

wherein each B independently represents an arylmethyl group having 7 to 21 carbon atoms, and each of W, A and H is as defined above for the formula (1).

The reaction of the formula (7) can be performed by appropriately modifying the conditions which are mentioned in connection with the reaction of the formula (6).

As in the case of the reaction of the formula (6), for obtaining the tetraacylhexaazaisowurtzitane in high yield by the reaction of the reaction formula (7), it is preferred to use as the reaction solvent the above-mentioned amide group-containing organic solvent.

Further, when it is intended to use the compound obtained by the reaction of the reaction formula (7) in the method of the present invention in which the distillative crystal deposition is employed, it is preferred that the reaction of the reaction formula (7) is performed using at least two reaction solvents which are the same as the first solvent and the second solvent to thereby obtain a reaction mixture containing the tetraacylhexaazaisowurtzitane, the first solvent and the second solvent, because such a reaction mixture as such can be used as the composition mixture to be subjected to distillative crystal deposition. When the reaction mixture obtained after completion of the reaction of the reaction formula (7) contains the first solvent, such a reaction mixture as such can be used as the above-mentioned composition system which is subjected to distillative crystal deposition. On the other hand, when a solvent which is the same as the first solvent is not used as a reaction solvent for the reaction of the reaction formula (7), it is preferred to add a solvent which is the same as the first solvent to ① the reaction system during the reaction of the reaction formula (7) or ② the reaction mixture obtained by the reaction of the reaction formula (7), to thereby obtain a mixture which can be used as the composition system to be subjected to distillative crystal deposition.

With respect to the amount of the solvent (which is the same as the first solvent) to be contained in the reaction mixture obtained by the reaction formula (7) which can be used as the composition system to be subjected to distillative crystal deposition, there is no particular limitation as long as the reaction mixture contains the solvent (which is the same as the first solvent) in an amount sufficient to dissolve the produced tetraacylhexaazaisowurtzitane. Therefore, the amount of the solvent (which is the same as the first solvent) varies depending on the amount of the compound of $WA_6$ as a starting material and the yield of the tetraacylhexaazaisowurtzitane. With respect to the weight ratio of the solvent (which is the same as the first solvent) to the solvent (which is the same as the second solvent) in the above-mentioned reaction mixture to be used as the composition mixture to be subjected to distillative crystal deposition, the weight ratio is generally in the range of from 0.1 to 10, preferably 0.2 to 5, more preferably 0.5 to 2.

Further preferred examples of tetraacylhexaazaisowurtzitanes (b) of the formula (1) include those in which n in the formula (1) is 6. Specific examples of these tetraacylhexaazaisowurtzitanes (b) include a hexaacylhexaazaisowurtzitane respectively represented by the following formula (8) and a tetraacyldiformylhexaazaisowurtzitanes represented by the following formula (9);

wherein each $F^r$ represents a formyl group, and each of W and A is as defined above for the formula (1).

For example, hexaacetylhexaazaisowurtzitane [compound of the formula (8)] and tetraacetyldiformylhexaazaisowurtzitane [compound of the formula (9)] are highly soluble in the above-mentioned first solvent (i.e., water and/or carboxylic acids). Therefore, these compounds can be advantageously used in the method of the present invention in which the distillative crystal deposition is conducted.

In the method of the present invention in which the distillative crystal deposition is conducted, when the above-mentioned hexaacetylhexaazaisowurtzitane or tetraacetyldiformylhexaazaisowurtzitane is used as the compound (b) in the composition system, it is preferred that water, formic acid or acetic acid is used as the first solvent, and that the above-mentioned ether group-containing organic solvent is used as the second solvent, in which hexaacetylhexaazaisowurtzitane and tetraacetyldiformylhexaazaisowurtzitane is sparingly soluble. Further, in the method of the present invention in which the distillative crystal deposition is conducted, when tetraacetyldiformylhexaazaisowurtzitane is used as compound (b) in the composition system, it is more preferred that formic acid is used as the first solvent because formic acid used as a formylating agent in the production of tetraacetyldiformylhexaazaisowurtzitane can be utilized as the first solvent.

When the desired compound in the method of the present invention is a hexaacylhexaazaisowurtzitane, it is preferred to use as compound (b) of the composition system a hexaacylhexaazaisowurtzitane which is obtained by subjecting a tetraacylbis(arylmethyl)hexaazaisowurtzitane to dearylmethylation and acylation as shown in the following reaction formula (10):

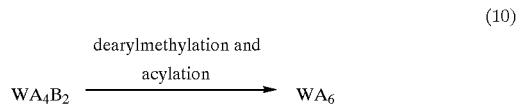

(10)

wherein each B independently represents an arylmethyl group having 7 to 21 carbon atoms, and each of W and A is as defined above for the formula (1).

In practicing the process of the formula (10) above, it is preferred to use a reaction method in which the tetraacylbis(arylmethyl)hexaazaisowurtzitane of the formula (4) is subjected to dearylmethylation to thereby synthesize a tetraacylhexaazaisowurtzitane, and the obtained tetraacylhexaazaisowurtzitane is then subjected to acetylation. This reaction method is preferred because by-production of alkyl group-containing compounds, such as a tetraacyldialkylhexaazaisowurtzitane, is suppressed.

When the desired compound of the process of the formula (10) above is a tetraacyldiformylhexaazaisowurtzitane, examples of reaction methods include a method in which the tetraacylbis(arylmethyl)hexaazaisowurtzitane of the formula (4) is subjected to dearylmethylation, to thereby synthesize a tetraacylhexaazaisowurtzitane, and the obtained tetraacylhexaazaisowurtzitane is then subjected to formylation, to thereby synthesize a tetraacyldiformylhexaazaisowurtzitane, and a method in which the tetraacylbis(arylmethyl)hexaazaisowurtzitane of the formula (4) is subjected to dearylmethylation and formylation simultaneously by adding formic acid to a reaction system for the dearylmethylation, thereby synthesizing a tetraacyldiformylhexaazaisowurtzitane.

In the process of the formula (10) above, it is preferred that each of the acyl groups of the desired compound is an acetyl group.

With respect to the reaction conditions for the dearylmethylation of the process of the formula (10), those which are mentioned in connection with the dearylmethylation of the process of the formula (5) above can be employed.

With respect to the acylating agent to be used in the process of the formula (10), the acylating agents which are mentioned in connection with the process of the formula (6) above can be used.

With respect to the synthesis of a hexaacylhexaazaisowurtzitane, preferred examples of acylating agents usable therefor include acyl halides, such as acetyl chloride, acetyl bromide and the like.

Examples of formylating agents usable for the synthesis of a tetraacyldiformylhexaazaisowurtzitane include formic acid; carboxylic anhydrides, such as formic anhydride and an anhydride of a mixture of acetic acid and formic acid; and formic esters, such as methyl formate. Among the above-mentioned formylating agents, formic acid is preferred because formic acid also functions as a reducing agent. Specifically, when formic acid is used as a solvent in the synthesis of the tetraacyldiformylhexaazaisowurtzitane, formic acid advantageously performs the following functions (a) to (c):

(a) function as a solvent which is highly capable of dissolving a tetraacylbis(arylmethyl)hexaazaisowurtzitane or a tetraacyldiformylhexaazaisowurtzitane;

(b) function as a reducing agent for reductive dearylmethylation; and (c) function as a formylating agent.

It is preferred that the second component of the reaction solvent to be used for the synthesis of tetraacyldiformylhexaazaisowurtzitane is an organic solvent capable of functioning as a second solvent in the distillative crystal deposition. With respect to the second solvent, there can be mentioned an organic solvent in which a tetraacyldiformylhexaazaisowurtzitane exhibits a solubility of 1% or less and which has a boiling point which is higher than that of the first solvent employed. Examples of such organic solvents include ether group-containing solvents, such as ethylene glycol diethyl ether, ethylene glycol di-n-butyl ether, diethylene glycol dimethyl ether, diethylene glycol diethyl ether and diethylene glycol dibutyl ether.

In the method of the present invention, it is especially preferred that a tetraacyldiformylhexaazaisowurtzitane to be subjected to distillative crystal deposition is obtained by the process of the following formula (11):

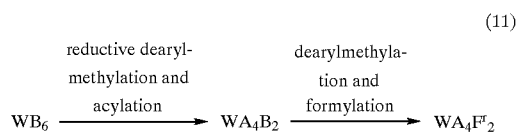

(11)

wherein $F^r$ represents a formyl group, each B independently represents an arylmethyl group having 7 to 21 carbon atoms, and each of W and A is as defined above for the formula (1) above.

As shown in the formula (11) above, in the first step of the process of the formula (11), a hexakis(arylmethyl)hexaazaisowurtzitane is subjected to reductive dearylmethylation in the presence of an acylating agent to thereby synthesize a tetraacylbis(arylmethyl)hexaazaisowurtzitane, and in the second step of the process, the tetraacylbis(arylmethyl)hexaazaisowurtzitane is subjected to dearylmethylation and formylation, either simultaneously or in this order, to thereby synthesize a tetraacyldiformylhexaazaisowurtzitane through a tetraacylhexaazaisowurtzitane. In the process of the formula (11) above, it is preferred that each of the acyl groups of the desired compound is an acetyl group.

With respect to the reaction conditions to be employed in the reductive dearylmethylation of a hexakis(arylmethyl)hexaazaisowurtzitane (which is conducted in the presence of an acylating agent) in the first step of the process of the formula (11), those which are mentioned in connection with the reductive dearylmethylation (which is conducted in the presence of an acylating agent) in the process of the formula (6) above can be employed. Among the reaction solvents mentioned in connection with the process of the formula (6), preferred in the first step of the process of the formula (11) is an amide group- or ether group-containing organic solvent which has a boiling point higher than that of formic acid and which serves as a second solvent in the composition system to be subjected to distillative crystal deposition.

With respect to the reaction conditions to be employed in the synthesis of a tetraacyldiformylhexaazaisowurtzitane from a tetraacylbis(arylmethyl)hexaazaisowurtzitane in the second step of the process of the formula (11), those which are mentioned in connection with the reductive dearylmethylation (which is conducted in the presence of an acylating agent) in the process of the formula (10) above can be employed.

As mentioned above, the distillative crystal deposition method can be advantageously used in the first aspect of the method of the present invention. However, as mentioned above, other crystal deposition methods, namely, membrane filtration separation method, adsorption method and chemical reaction method, can also be used. These other methods are explained below in more detail.

The membrane filtration separation method (method B) is explained in detail below.

The membrane filtration separation method, which is a method for removing the first solvent from the composition system to deposit crystals of the desired compound, employs a separation membrane having a selective permeability for the first solvent. When the removal of the first solvent is performed by using the membrane separation method, it is most preferred that the first solvent is water. The type of the separation membrane to be used for separating water from the composition system can be selected in accordance with various factors, such as the shape of the reactor and the like. As examples of separation membranes, there can be mentioned conventional separation membranes for separating water from ethanol. Specific examples of such separation membranes include a polyhydroxymethylene membrane; an acrylic acid-acrylonitrile copolymer membrane; an ionized chitosan membrane; organic membranes, such as a composite membrane having an active layer of maleic acid-crosslinked PVA, and a polymer alloy membrane (see Unexamined Japanese Patent Application Laid-Open Specification Nos. 59-109204 and 60-129104); and an inorganic membrane, such as an Azeolite membrane described in "Kagakukougaku Sinpojyumu Siriizu (Chemical Engineering Symposium Series)" 41, p. 102–105 (1994). From the viewpoint of the commercial practice of the method of the present invention by using the membrane filtration separation method, it is preferred to use a membrane having an excellent durability, high resistance against the chemicals contained in a reaction system and a reaction mixture, and high mechanical strength. An example of such a preferred membrane is an inorganic membrane since it generally has a high operation limit temperature and high chemical resistance. The above-mentioned A-zeolite membrane can be prepared in accordance with a method described in "Kagakukougaku Sinpojyumu Siriizu (Chemical Engineering Symposium Series)" 41, p. 102–105 (1994), that is, a method in which a porous alumina substrate having a pore diameter of approximately 1 mm is immersed in a solution containing sodium silicate, sodium hydroxide, sodium aluminate and aluminum hydroxide in weight ratios of $H_2O/Na_2O=60$, $Na_2O/SiO_2=1$, and $SiO_2/Al_2O_3=2$, and then subjected to hydrothermal reaction at 80 to 100° C. for 3 to 12 hours. The properties of the membrane can be controlled by repeating the above-mentioned immersion and hydrothermal reaction.

The morphology of the separation membrane is not particularly limited, and a separation membrane having a desired morphology can be obtained by using a substrate having the desired morphology. The morphology of the separation membrane can be selected in accordance with the construction of the reactor to be used. For example, a sheet type membrane, a module produced using a sheet type membrane, a tubular membrane and a module produced using a tubular membrane are generally used.

With respect to the temperature for performing the removal of water as the first solvent, a high temperature is advantageous for increasing the water permeability of the separation membrane, and a low temperature is advantageous for increasing the water-separation precision of the separation membrane. The temperature for performing the removal of water can be selected within the range of from room temperature to 200° C. When the separation membrane is incorporated in the reactor, the temperature for the membrane separation is selected within the reaction temperature, which is usually within the range of from 40 to 165° C., preferably from 40 to 100° C.

The separation of water from the composition system is theoretically possible as long as a transmembrane pressure difference is present in the membrane, and the separation pressure is generally in the range of from 0.5 to 20 kg/cm². In addition, water is effectively removed from the composition system by evacuating the downstream side of the separation membrane, as viewed in the flow direction of water.

The adsorption method (method C) is explained in detail below.

The adsorption method, which is a method for removing the first solvent from the composition system to deposit crystals of the desired compound, comprises adsorbing the first solvent on an adsorbent. With respect to this method, the following points (a) and (b) should be noted:

(a) When the first solvent is water, as the adsorbent, there can be mentioned, for example, a molecular sieve (in which pores serve to adsorb water molecules); and salts, such as calcium chloride, magnesium sulfate and the like (which are capable of forming stable hydrates with water molecules).

(b) When the first solvent is a carboxylic acid, as the adsorbent, there can be mentioned, for example, amine type anion exchange resins and the like which are capable of adsorbing a carboxylic anion.

The chemical reaction method (method D) is explained in detail below.

The chemical method, which is a method for removing the first solvent from the composition system to deposit crystals of the desired compound, comprises converting the first solvent into a different substance by a chemical reaction. With respect to this method, the following points (a) and (b) should be noted:

(a) When the first solvent is water, the water is reacted with a substance which reacts vigorously with water, such as potassium, sodium, lithium aluminum hydride, sodium borohydride or calcium borohydride, to thereby convert the substance into a metal hydroxide.

(b) When the first solvent is a carboxylic acid, the carboxylic acid is reacted with a basic compound, such as an amine or a metal hydride, to thereby form a salt, and the salt is then subjected to either a dehydration reaction with an alcohol to thereby form an ester, or a dehydration reaction with an amine to thereby form an amide. With respect to water by-produced by the above-mentioned dehydration reactions, the by-produced water can be removed by any of the above-mentioned removal methods, that is, A. distillation, B. membrane filtration separation, C. adsorption and D. chemical reaction.

With respect to the method for isolating the deposited crystals from the composition system in step (III), there is no particular limitation.

2. The method of the second aspect:

In step (A) of the method of the second aspect of the present invention, there is provided a composition system comprising;

(a') a mixed solvent of water and at least one organic solvent which is phase-separable from water, and (b') an acyl group-containing hexaazaisowurtzitane derivative represented by the following formula (12):

$$WA_nH_{(6-n)} \qquad (12)$$

wherein n represents an integer of 4 or 6, each A independently represents an acyl group having 1 to 10 carbon atoms, H represents a hydrogen atom, and W represents a hexavalent hexaazaisowurtzitane residue represented by the following formula (13):

(13)

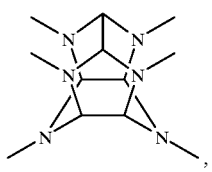

wherein the composition system comprises an organic phase and an aqueous phase having dissolved therein at least a part of the acyl group-containing hexaazaisowurtzitane derivative (b').

In step (B) of the method of the second aspect of the present invention, the aqueous phase is separated from the composition system.

In step (C) of the method of the second aspect of the present invention, the water of the aqueous phase is evaporated to obtain the hexaazaisowurtzitane derivative (b') in isolated form.

As apparent from above, the method of the second aspect of the present invention is substantially the same as the above-mentioned method of the first aspect of the present invention, except that a mixed solvent (a') of water and at least one organic solvent which is phase-separable from water is necessarily used, and that the desired compound [the acyl group-containing hexaazaisowurtzitane derivative (b')] is obtained by evaporating the water of the separated aqueous phase.

In the method of the second aspect of the present invention, the acyl group-containing hexaazaisowurtzitane derivative (b') of the formula (12) is the same as the acyl group-containing hexaazaisowurtzitane derivative (b) of the formula (1) used in the method of the first aspect, and the hexavalent hexaazaisowurtzitane residue of the formula (13) is the same as the hexavalent hexaazaisowurtzitane residue of the formula (2) mentioned in connection with the method of the first aspect.

With respect to the mixed solvent (a') used in the method of the second aspect, there is no particular limitation, as long as the above-mentioned organic solvent is phase-separable from water.

With respect to the organic solvent used in the mixed solvent (a'), which is phase-separable from water, it is preferred to use an organic solvent in which the acyl group-containing hexaazaisowurtzitane derivative (b') of the formula (12) exhibits a solubility of 0.5% by weight or less. Examples of organic solvents used in the mixed solvent (a') include ester solvents, such as ethyl acetate and butyl acetate; ether solvents, such as diethyl ether and diisopropylether; halogen-containing solvents, such as chloroform and dichloromethane; and aromatic solvents, such as benzene, toluene and xylene.

With respect to the specific examples of the acyl group-containing hexaazaisowurtzitane derivatives (b'), the same compounds mentioned above as specific examples of the compounds (b) of the formula (1) can be mentioned. Further, with respect to the method for the synthesis of the compounds (b'), the conditions for the synthesis, the materials used for the synthesis, the amounts of the materials and the like, those which are mentioned above in connection with the compounds (b) of the formula (b) can be employed.

With respect to the method for separating the aqueous phase from the composition system and the method for evaporating the water of the aqueous phase, there is no particular limitation.

Hereinbelow, explanation is made with respect to the structures of the above-mentioned compounds $WB_6$, $WA_4B_2$, $WA_4H_2$ and $WA_4F'_2$.

The arylmethyl group represented by B in each of the reaction formulae (5), (6), (7), (10) and (11) means an aryl group (Ar)-substituted methyl group which generally has 7 to 21 carbon atoms. As a representative example of arylmethyl groups B, there can be mentioned a group having a structure represented by the following formula (14):

wherein Ar represents an aryl group having 6 to 20 carbon atoms.

As mentioned above, the number of carbon atoms of the Ar in the formula (14) above is generally in the range of from 6 to 20, preferably from 6 to 10, most preferably 6. Examples of Ar's include a phenyl group; alkylphenyl groups, such as a tolyl group (o-, m- and p-isomers), an ethylphenyl group (o-, m- and p-isomers), and a xylyl group; alkoxyphenyl groups, such as a methoxyphenyl group (o-, m- and p-isomers), an ethoxyphenyl group (o-, m- and p-isomers), and a butoxyphenyl group (o-, m- and p-isomers); and unsubstituted and substituted naphthyl groups. Of these, preferred are a phenyl group and alkoxyphenyl groups. In the $WB_6$, the six arylmethyl groups may be the same or deferent.

With respect to the compound represented by the formula $WA_4B_2$ in the reaction formulae (5), (6), (10) and (11) above, it can assume a plurality of stereoisomeric configurations which are different in the positions of the acyl groups and the arylmethyl groups. The compound represented by the formula $WA_4B_2$ to be used in the present invention may be any of the stereoisomers represented by the following formulae (15-1) to (15-6):

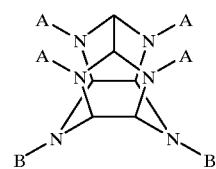
(15-1)

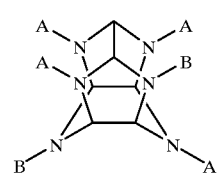
(15-2)

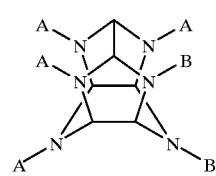
(15-3)

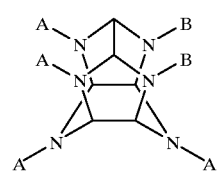
(15-4)

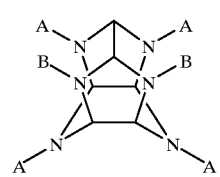
(15-5)

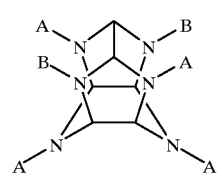
(15-6)

wherein each of A and W is as defined above for the formula (12) above and B is as defined above, and the optical isomers thereof.

Of these compounds, most preferred is the compound of the formula (15-1) above since it can provide a most hydrophilic structure when each of the two arylmethyl groups (each represented by B) is replaced by a hydrogen atom.

With respect to the hexaazaisowurtzitane derivative represented by the formula $WA_4H_2$ in the formulae (3), (5) and (7) above, it can assume a plurality of stereoisomeric configurations which are different in the positions of the acyl groups and the hydrogen atoms. The hexaazaisowurtzitane derivative represented by $WA_4B_2$ which is produced by the synthesis process used in the present invention may be any of the stereoisomers. Specifically, these stereoisomers are the hexaazaisowurtzitane derivatives represented by the formulae (15-1) to (15-6) above wherein each of the arylmethyl groups is replaced by a hydrogen atom. Of these, most preferred is the hexaazaisowurtzitane derivative represented by the formula (15-1) above wherein each of the arylmethyl groups is replaced by a hydrogen atom, since it has very high hydrophilicity.

Further, with respect to the tetraacetyldiformylhexaazaisowurtzitane represented by the formula (9) above (wherein A represents an acetyl group), which is a desired compound for the distillative crystal deposition, it can assume a plurality of stereoisomeric configurations which are different in the positions of the acetyl groups and the formyl groups. The tetraacetyldiformylhexaazaisowurtzitane produced by the synthesis process used in the present invention may be any of the stereoisomers. Specifically, these stereoisomers are the hexaazaisowurtzitane derivatives represented by the formulae (15-1) to (15-6) above wherein each of the arylmethyl groups is replaced by a formyl group and each of the acyl groups is an acetyl group. Of these, most preferred is the hexaazaisowurtzitane derivative represented by the formula (15-1) above wherein each of the arylmethyl groups is replaced by a formyl group and each of the acyl groups is an acetyl group since, it has very high hydrophilicity.

The reactions represented by the formulae (6), (7) and (11) above are described below.

Each of the above-mentioned reactions comprises steps of: 1) subjecting $WB_6$ to reductive dearylmethylation in the presence of an acylating agent so as to convert the N-arylmethyl group contained therein to an N—H group; and 2) subsequently subjecting the resultant to acylation so as to convert the N—H group to an N-acyl group. In addition, since an N-alkyl group may be formed by the reduction (as a side reaction) of an N-acyl group, which reduction may occur depending on the reaction conditions, a by-produced, N-alkyl group-containing hexaazaisowurtzitane derivative is produced. The reaction routes of the formulae (6), (7) and (11) above have been presumed from the reaction products, and the presumed routes are shown in the chart of the following formula (16):

(16)

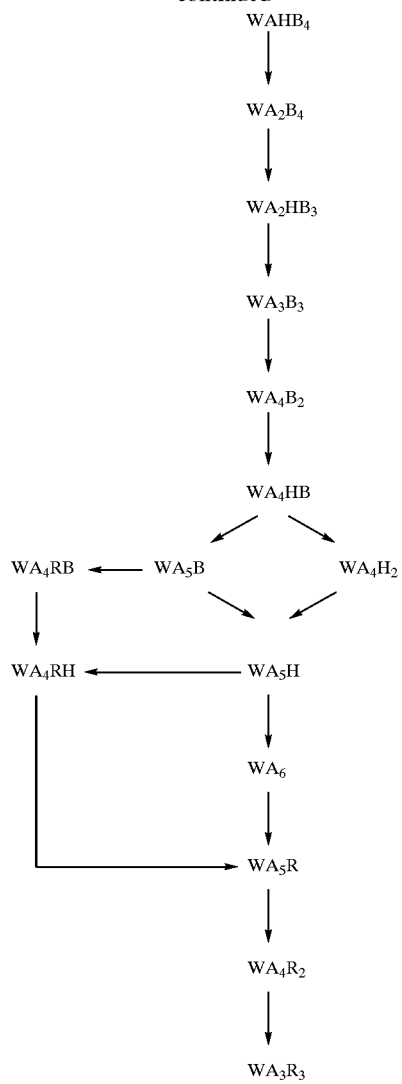

wherein, B represents an arylmethyl group having 7 to 21 carbon atoms; each R independently represents an alkyl group having 1 to 10 carbon atoms; and each of W, A and H is as defined above for the formula (1) above.

Any of the compounds shown in the chart of the formula (16) above may be contained in the compound of the formula (1) above and in the products obtained by the reactions of the formulae (5), (6), (7), (10) and (11) above.

The method of the present invention for producing an acyl group-containing hexaazaisowurtzitane derivative is commercially advantageous in that an acyl group-containing hexaazaisowurtzitane derivative can be easily obtained in high purity form in high yield and at low cost, by the removal of the first solvent (water or a carboxylic acid) from the composition system or by the removal of the first solvent by evaporation from the first solvent phase (which has been phase separated from the second solvent phase) in which at least a part of the acyl group-containing hexaazaisowurtzitane derivative is dissolved.

The reaction routes involved in the method of the present invention are summarized in the following chart.

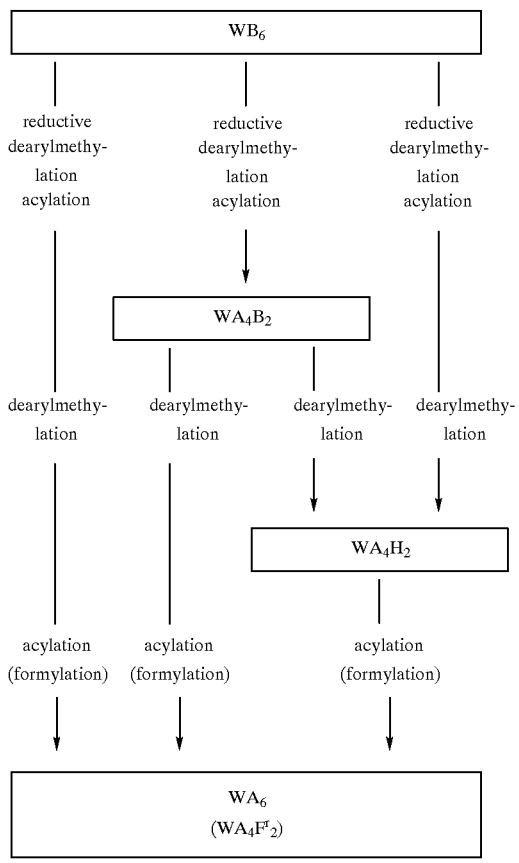

BEST MODE FOR CARRYING OUT THE INVENTION

Hereinbelow, the present invention is described in more detail with reference to Examples and Reference Example, which should not be construed as limiting the scope of the present invention.

In the Examples, various measurements were conducted in accordance with the following methods.

(1) Quantitative analysis of tetraacetylhexaazaisowurtzitane and hexaacetylhexaazaisowurtzitane by high performance liquid chromatography (HPLC):

Measurement was conducted under the following conditions by the below-described apparatus.

i) Apparatus

HPLC apparatus: LC-10A (manufactured and sold by Shimadzu Corporation, Japan)

Column: TSK-GEL AMIDE-80 4.6×250 mm (manufactured and sold by TOSOH, Japan)

ii) Conditions

Detection: UV (210 nm)

Column temperature: 40° C.

Mobile phase: tetrahydrofuran/$H_2O$ (90/10) (v/v)

Flow rate: 1 ml/min

The amount of sample per injection: 10 µl

The samples to be subjected to HPLC analysis were prepared by the following methods.

(i) The method for preparing a sample from a reaction mixture obtained by the reductive dearylmethylation of $WB_6$ in the presence of an acylating agent:

0.5 ml of the reaction mixture (a slurry containing a catalyst) was subjected to evaporation under reduced pressure to thereby remove the liquid component of the reaction mixture to obtain a residue. 9.5 ml of water was added to the residue, and stirred vigorously and then subjected to filtration to remove the catalyst to thereby obtain a filtrate. The filtrate was used as a sample for HPLC.

(ii) The method for preparing a sample from a reaction mixture obtained by the reductive dearylmethylation of $WA_4B_2$:

The reaction mixture was subjected to filtration to remove the catalyst to thereby obtain a filtrate. 0.5 ml of the filtrate was subjected to evaporation under reduced pressure to thereby remove the liquid component to obtain a residue. 9.5 ml of water was added to the residue, and stirred vigorously and subjected to filtration to remove the insolubles to thereby obtain a filtrate. The filtrate was used as a sample for HPLC.

(2) Quantitative analysis of tetraacetyldiformylhexaazaisowurtzitane by HPLC:

Measurement was conducted under the following conditions by the below-described apparatus.

i) Apparatus

HPLC apparatus: LC-10A (manufactured and sold by Shimadzu Corporation, Japan)

Column: L-Column ODS 4.6×250 mm (manufactured and sold by Chemicals Inspection & Testing Institute, Japan)

ii) Conditions

Detection: UV (210 nm)

Column temperature: 40° C.

Mobile phase: acetonitrile/$H_2O$ (5/95) (v/v)

Flow rate: 1 ml/min

The amount of sample per injection: 10 µl

The samples to be subjected to HPLC analysis were prepared by the following method.

A reaction mixture containing tetracetyldiformylhexaazaisowurtzitane was subjected to filtration to remove the catalyst to thereby obtain a filtrate. 0.5 ml of the filtrate was subjected to evaporation under reduced pressure to thereby remove the liquid component to obtain a residue. 9.5 ml of water was added to the residue, and stirred vigorously and subjected to filtration to remove the insolubles to thereby obtain a filtrate. The filtrate was used as a sample for HPLC.

(3) Quantitative analysis of other hexaazaisowurtzitane derivatives by gas chromatography (GC):

Measurement was conducted under the following conditions by the below-described apparatus.

i) Apparatus

GC apparatus: GC-14B (manufactured and sold by Shimadzu Corporation, Japan)

Column: Metallic capillary column, Ultra Alloy (HT), 0.25 mm(inner diameter)×15 m, thickness of film coated on the inner wall of the capillary column: 0.15 µm ii) Conditions Detection: FID Temperature:
  Inlet: 340° C.
  Column: maintained at 200° C. for 1 minute, and elevated to 340° C. at a temperature elevation rate of 15° C./min and maintained at 340° C. for 4 minutes.

Detector: 340° C.

Carrier gas: N₂ Total flow: 100 ml/min

The amount of sample per injection: 5 µl

Tricosane was used as an internal standard.

The samples to be subjected to GC analysis were prepared by the following method.

23.5 ml of chloroform was added to 0.5 ml of a reaction mixture containing a hexaazaisowurtzitane to obtain a solution. To 4 ml of the solution was added 0.5 ml of a solution prepared by dissolving 0.1 g of tricosane in 100 ml of chloroform, and the resultant mixture was used as a sample for GC.

Reference Example [Solubilities of various types of acyl group-containing hexaazaisowurtzitane derivatives in various types of solvents]

The solubilities of various types of acyl group-containing hexaazaisowurtzitane derivatives in various types of solvents were examined. The results are shown in Table 1.

various types of mixed solvents of a first solvent and a second solvent]

Each of various types of acyl group-containing hexaazaisowurtzitane derivatives was individually dissolved in a mixed solvent of first and second solvents to obtain a composition system. Then, the first solvent was distilled off from the composition system to deposit crystals of the hexaazaisowurtzitane derivative. The respective amounts (g) of the first and second solvents employed and the results of the distillative crystal deposition are shown in Table 2. In Example 1, the distillation for crystal deposition was performed to an extent such that the content of the first solvent became 1% by weight or less, based on the total weight of the first and second solvents.

TABLE 1

Solubilities of various types of acyl group-containing hexaazaisowurtzitane derivatives in various solvents at room temperature

| | | | Desired compound | | | Unreacted compound | By-product |
|---|---|---|---|---|---|---|---|
| | | | $WA_4H_2$ | $WA_6$ | $WA_4F^r_2$ | $WA_4B_2$ | $WA_4E_2$ |
| First solvent | | Water | >3% | >1% | >5% | <0.1% | >4% |
| | | Formic acid | >20% | >30% | >30% | >50% | >4% |
| | | Acetic acid | >1% | >2% | >10% | >10% | >4% |
| Second solvent | Amide group-containing solvents | DMAc | <0.1% | | | >0.2% | >3% |
| | | DMF | <0.1% | | | >0.2% | >3% |
| | | DMI | <0.1% | | | >0.2% | >3% |
| | | NMP | <0.1% | | | >0.2% | >3% |
| | Ether group-containing solvents | EDE | <0.1% | | <0.1% | <0.5% | >0.5% |
| | | EDB | <0.1% | <0.1% | <0.1% | <0.5% | >0.5% |
| | | DEDM | <0.1% | <0.1% | <0.1% | <0.5% | >0.5% |
| | | DEDE | <0.1% | <0.1% | <0.1% | <0.5% | >0.5% |
| | | DEDB | <0.1% | <0.1% | <0.1% | <0.5% | >0.5% |

The abbreviations used in Table 1 represent the respective compounds described below.

$WA_4H_2$: tetraacetylhexaazaisowurtzitane $WA_6$: hexaacetylhexaazaisowurtzitane $WA_4F^r_2$: tetraacetyldiformylhhexaazaisowurtzitane $WA_4B_2$: tetraacetyldibenzylhexaazaisowurtzitane $WA_4E_2$: tetraacetyldiethylhexaazaisowurtzitane DMAc: N,N-dimethylacetamide DMF: N,N-dimethylformamide DMI: 1,3-dimethyl-2-pyrrolidone NMP: N-methyl-2-prrolidone EDE: ethylene glycol diethyl ether EDB: ethylene glycol di-n-butyl ether DEDM: diethylene glycol dimethyl ether DEDE: diethylene glycol diethyl ether DEDB: diethylene glycol dibutyl ether

EXAMPLE 1

[Distillative crystal deposition of various types of acyl group-containing hexaazaisowurtzitane derivatives from

TABLE 2

Results of crystal deposition of various type of acyl group-containing hexaazaisowurtzitane derivatives

| Desired compound | | First solvent | | Second solvent | | Result |
|---|---|---|---|---|---|---|
| Material | Amount (g) | Solvent | Amount (g) | Solvent | Amount (g) | Yield (%) |
| $WA_4H_2$ | 1 | Water | 40 | DMAc | 20 | 98 |
| $WA_4H_2$ | 1 | Acetic acid | 40 | DEDE | 20 | 98 |
| $WA_4H_2$ | 1 | Water | 40 | DEDM | 20 | 97 |
| $WA_4H_2$ | 1 | Water | 40 | DMF | 20 | 97 |
| $WA_6$ | 1 | Formic acid | 40 | EDE | 20 | 96 |
| $WA_6$ | 1 | Water | 40 | DEDE | 20 | 97 |
| $WA_4F^r_2$ | 1 | Formic acid | 40 | EDB | 20 | 95 |
| $WA_4F^r_2$ | 1 | Water | 40 | DEDM | 20 | 98 |

The abbreviations used in Table 2 represent the respective compounds described below.

$WA_4H_2$: tetraacetylhexaazaisowurtzitane $WA_6$: hexaacetylhexaazaisowurtzitane $WA_4F^r_2$: tetraacetyldiformylhexaazaisowurtzitane DMAc: N,N-dimethylacetamide DMF: N,N-dimethylformamide
EDE: ethylene glycol diethyl ether
EDB: ethylene glycol di-n-butyl ether
DEDM: diethylene glycol dimethyl ether
DEDE : diethylene glycol diethyl ether

EXAMPLE 2

[Distillative crystal deposition of $WA_4H_2$ obtained by the reactions of the reaction scheme: $WB_6 \rightarrow WA_4B_2 \rightarrow WA_4H_2$] [first solvent: water; second solvent: N,N-dimethylacetamide (DMAc)]

2.1 g of hexabenzylhexaazaisowurtzitane, 3.15 g of 10% Pd—C (as a catalyst), 1.84 g of acetic anhydride and 30 ml of DMAc were charged into a 100 ml autoclave and the autoclave was closed. The autoclave was purged with nitrogen gas. Then, hydrogen gas was introduced into the autoclave so that the internal pressure of the autoclave became 1.1 kgf/cm$^2$.

The stirring of the content of the autoclave was started at a stirring rate of 700 rpm or more and the internal temperature of the autoclave was elevated to 60° C. to perform a reaction. During the reaction, hydrogen gas was continuously introduced into the autoclave so that the internal pressure of the autoclave was kept at 1.1 kgf/cm$^2$. After 3 hours from the start of the reaction, the analysis of the reaction system by GC showed that the yield of tetraacetyldibenzylhexaazaisowurtzitane reached about 60%, based on the hexabenzylhexaazaisowurtzitane. Then, the reaction was terminated and the obtained reaction mixture was taken out from the autoclave and the catalyst contained in the reaction mixture was filtered off to thereby obtain a solution.

The obtained solution, 3.15 g of 10% Pd—C (as a catalyst) and 30 ml of water were charged into a 100 ml autoclave and the autoclave was closed. The autoclave was purged with nitrogen gas. Then, hydrogen gas was introduced into the autoclave so that the internal pressure of the autoclave became 3.3 kgf/cm$^2$.

The stirring of the content of the autoclave was started at a stirring rate of 700 rpm or more and the internal temperature of the autoclave was elevated to 130° C. to perform a reaction. During the reaction, hydrogen gas was continuously introduced into the autoclave so that the internal pressure of the autoclave was kept at 3.3 kgf/cm$^2$. After 1 hour from the start of the reaction, the analysis of the reaction system by HPLC showed that the yield of tetraacetylhexaazaisowurtzitane reached about 60%, based on the hexabenzylhexaazaisowurtzitane (the yield of this reaction varied in the range of from 58 to 68%). Then, the reaction was terminated and the obtained reaction mixture was taken out from the autoclave and the catalyst contained in the reaction mixture was filtered off to thereby obtain a solution.

The above-mentioned series of reactions were repeated 10 times and all of the obtained solutions were mixed together to obtain a mixed solution.

The mixed solution was subjected to distillation (70° C., 1 mmHg) using a rotary evaporator equipped with a constant temperature bath, a vacuum pump and a vacuum controller, to remove the solvent, thereby obtaining 17.0 g of a viscous slurry (the content of tetraacetylhexaazaisowurtzitane: 56.8% by weight).

5.0 g of the slurry was dissolved into a mixed solvent of 15 ml of DMAc and 150 ml of water to thereby obtain a solution. The solution was charged into a 300 ml egg plant flask and subjected to distillation (70° C., 50 mmHg) using a rotary evaporator equipped with a constant temperature bath, a vacuum pump and a vacuum controller, to thereby remove about 150 ml of water. After the distillation, the egg plant flask was disconnected from the rotary evaporator, and the resultant distillation residue in the egg plant flask was allowed to cool to room temperature and stand for 6 hours at room temperature, thereby depositing solids.

The deposited solids were collected by suction filtration and then washed with 10 ml of DMAc to thereby obtain a wet solid substance. The wet solid substance was subjected to drying by means of a vacuum dryer (70° C., 1 mmHg) to thereby obtain 2.51 g of tetraacetylhexaazaisowurtzitane as a white solid [crystal deposition yield: 88%; purity: 98% (determined by HPLC)].

EXAMPLE 3

[High yield isolation of $WA_4H_2$ by distillative crystal deposition of $WA_4H_2$ obtained by the reactions of the reaction scheme: $WB_6 \rightarrow WA_4B_2 \rightarrow WA_4H_2$]

0.84 g of 10% Pd—C (as a catalyst) was charged into a 100 ml autoclave, and the autoclave was purged with hydrogen gas so that the internal pressure of the autoclave became 1.1 kgf/cm$^2$. Then, the content of the autoclave was stirred at a stirring rate of 50 rpm at 60° C. for 2 hours. A solution obtained by dissolving 2.1 g of hexabenzylhexaazaisowurtzitane and 1.82 g of acetic anhydride in 30 ml of DMAc was quickly charged into the autoclave by means of a syringe, and the stirring rate was immediately elevated to 700 rpm, and a reaction was performed at a temperature of 60° C. for 1 hour. During the reaction, hydrogen gas was continuously introduced into the autoclave so that the internal pressure of the autoclave was kept at 1.1 kgf/cm$^2$. By the above-mentioned reaction, tetraacetyldibenzylhexaazaisowurtzitane (containing tetraacetylhexaazaisowurtzitane) was produced. Hereinafter, this reaction is referred to as the "first-stage reaction". After the first-stage reaction, 30 ml of water was charged into the autoclave by means of a syringe, and hydrogen gas was introduced into the autoclave so that the internal pressure of the autoclave was kept at 9 kgf/cm$^2$, and the reaction temperature was elevated to 90° C., and the stirring at 700 rpm was further continued for 1 hour to perform a reaction for 1 hour to effect debenzylation. After that period of time, the reaction was terminated and the obtained reaction mixture was taken out from the autoclave and the catalyst contained in the reaction mixture was filtered off to thereby obtain a solution. The analysis of this solution by HPLC showed that the solution contained 0.80 g of tetraacetylhexaazaisowurtzitane and the yield thereof reached 80%. Hereinafter, this debenzylation reaction is referred to as the "second-stage reaction".

The solution was charged into an egg plant flask and subjected to distillation (50° C., 10 mmHg) using a rotary evaporator equipped with a constant temperature bath, a vacuum pump and a vacuum controller, to thereby remove about 32 ml of low boiling point fractions (such as water and toluene) having a boiling point which is lower than that of DMAc. After the distillation, the egg plant flask was disconnected from the rotary evaporator, and the resultant distillation residue in the egg plant flask was allowed to cool to room temperature, thereby depositing solids.

The deposited solids were collected by suction filtration and then washed with about 1 ml of DMAc to thereby obtain a wet solid substance. The wet solid substance was subjected to drying by means of a vacuum dryer (70° C., 1 mmHg or less) to thereby obtain 0.775 g of tetraacetylhexaazaisowurtzitane as a white solid [crystal deposition yield: 97%; purity: 98% (determined by HPLC)].

EXAMPLE 4

[Distillative crystal deposition of $WA_4H_2$ obtained by the reactions of the reaction scheme: $WB_6 \rightarrow WA_4B_2 \rightarrow WA_4H_2$] [first solvent: acetic acid; second solvent: diethyleneglycol diethyl ether]

Substantially the same procedure as described in Example 3 was repeated except that, as the reaction solvent for the first-stage reaction, diethyleneglycol diethyl ether was used instead of DMAc, that the reaction time for the first-stage reaction was changed from 1 hour to 10 hours, and that, as a first solvent which was added to the reaction system at a point in time between the first-stage reaction and the second-stage reaction, acetic acid was used instead of water. As a result, the yield of tetraacetylhexaazaisowurtzitane was 72%, based on the hexabenzylhexaazaisowurtzitane [crystal deposition yield: 96%; purity: 97% (determined by HPLC)].

EXAMPLE 5

[Distillative crystal deposition of $WA_4H_2$ obtained by the reaction of the reaction scheme: $WA_4B_2 \rightarrow WA_4H_2$] [first solvent: acetic acid; second solvent: diethylene glycol dimethyl ether]

1.22 g of tetraacetyldibenzylhexaazaisowurtzitane, 0.84 g of 10% Pd—C (as a catalyst) which had been reduced with hydrazine, and a mixed solvent of 30 ml of acetic acid and 30 ml of diethylene glycol dimethyl ether (as a reaction solvent) were charged into a 100 ml autoclave and the autoclave was closed. The autoclave was purged with nitrogen gas. Then, hydrogen gas was introduced into the autoclave so that the internal pressure of the autoclave became 9 kgf/cm$^2$.

The stirring of the content of the autoclave was started at a stirring rate of 700 rpm and the internal temperature of the autoclave was elevated to 90° C. to perform a reaction for 1 hour. The analysis of the reaction system by HPLC showed that the yield of tetraacetylhexaazaisowurtzitane was 95%, based on the tetraacetyldibenzylhexaazaisowurtzitane.

Then, the reaction was terminated and the resultant reaction mixture was taken out from the autoclave and the catalyst contained in the reaction mixture was filtered off to thereby obtain a solution as a filtrate. The solution was subjected to distillative crystal deposition in substantially the same manner as described in Example 3, to thereby obtain crystals of tetraacetylhexaazaisowurtzitane [crystal deposition yield: 95%; purity: 99% (determined by HPLC)].

EXAMPLE 6

[Distillative crystal deposition of $WA_4H_2$ obtained by the reaction of the reaction scheme: $WA_4B_2 \rightarrow WA_4H_2$] [first solvent: acetic acid; second solvent: ethylene glycol di-n-butyl ether (added after the reaction)]

Substantially the same reaction as described in Example 5 was repeated except that 30 ml of acetic acid was solely used as the reaction solvent. After the reaction, the resultant reaction mixture was taken out from the autoclave and the catalyst contained in the reaction mixture was filtered off to thereby obtain a solution as a filtrate. 30 ml of ethylene glycol di-n-butyl ether was added to the solution, and then stirred to obtain a homogeneous solution. The homogeneous solution was subjected to distillative crystal deposition in substantially the same manner as described in Example 3, to thereby obtain crystals of tetraacetylhexaazaisowurtzitane. As a result, the yield of tetraacetylhexaazaisowurtzitane was 87%, based on the tetraacetyldibenzylhexaazaisowurtzitane [crystal deposition yield: 94%; purity: 99% (determined by HPLC)].

EXAMPLE 7

[Distillative crystal deposition of $WA_4H_2$ obtained by the reaction of the reaction scheme: $WA_4B_2 \rightarrow WA_4H_2$] [first solvent: acetic acid+water; second solvent: diethylene glycol diethyl ether]

Substantially the same reaction and distillative crystal deposition as described in Example 5 were repeated except that a mixed solvent of 20 ml of acetic acid and 10 ml of water was used as the reaction solvent. As a result, the yield of tetraacetylhexaazaisowurtzitane was 81%, based on the tetraacetyldibenzylhexaazaisowurtzitane [crystal deposition yield: 96%; purity: 97% (determined by HPLC)].

EXAMPLE 8

[Distillative crystal deposition of $WA_4H_2$ obtained by the reactions of the reaction scheme: $WB_6 \rightarrow WA_4B_2 \rightarrow WA_4H_2$] [first solvent: acetic acid; second solvent: diethylene glycol diethyl ether+diethylene glycol dimethyl ether]

Substantially the same procedure as described in Example 3 was repeated except that a mixed solvent of 15 ml of diethylene glycol diethyl ether and 15 ml of diethylene glycol dimethyl ether was used as the reaction solvent for the first-stage reaction, that the reaction time for the first-stage reaction was changed from 1 hour to 10 hours, and that, as a first solvent which was added to the reaction system at a point in time between the first-stage reaction and the second-stage reaction, acetic acid was used instead of water. As a result, the yield of tetraacetylhexaazaisowurtzitane was 69%, based on the hexabenzylhexaazaisowurtzitane [crystal deposition yield: 95%; purity: 98% (determined by HPLC)].

EXAMPLE 9

[Distillative crystal deposition of $WA_4H_2$ obtained by the reaction of the reaction scheme: $WB_6 \rightarrow WA_4H_2$] [first solvent: water (added after the reaction); second solvent: DMAc]

Substantially the same first-stage reaction as described in Example 3 was repeated except that the amount of 10% Pd—C (as a catalyst) was changed to 3.15 g and that the reaction time was changed to 3 hours, to thereby obtain a reaction mixture containing deposited tetraacetylhexaazaisowurtzitane.

The analysis of the reaction mixture by HPLC showed that the yield of tetraacetylhexaazaisowurtzitane reached 60%, based on the hexabenzylhexaazaisowurtzitane.

30 ml of water was added to the reaction mixture and stirred at 40° C. for 30 minutes to dissolve the deposited tetraacetylhexaazaisowurtzitane. Then, the catalyst contained in the reaction mixture was filtered off to thereby obtain a solution as a filtrate.

The solution was subjected to distillative crystal deposition in substantially the same manner as described in Example 3, to thereby obtain crystals of tetraacetylhexaazaisowurtzitane [crystal deposition yield: 98%; purity: 99% (determined by HPLC)].

EXAMPLE 10

[Distillative crystal deposition of $WA_6$ obtained by the reactions of the reaction scheme: $WA_4B_2 \rightarrow WA_4H_2 \rightarrow WA_6$] [first solvent: acetic acid; second solvent: diethylene glycol diethyl ether]

Substantially the same reaction as described in Example 5 was repeated except that diethylene glycol diethyl ether was used as the reaction solvent. The resultant reaction mixture was taken out from the autoclave and the catalyst contained in the reaction mixture was filtered off to thereby obtain a solution as a filtrate. 2 g of acetyl chloride was added to the solution and stirred at room temperature for 1 hour to perform a reaction. By this reaction, the N—H groups of tetraacetylhexaazaisowurtzitane were acetylated, so that hexaacetylhexaazaisowurtzitane was obtained in an approximately stoichiometric amount, based on the tetraacetyldibenzylhexaazaisowurtzitane. The resultant reaction mixture was subjected to distillative crystal deposition in substantially the same manner as described in Example 3, to thereby obtain crystals of hexaacetylhexaazaisowurtzitane in a yield of 90%, based on the tetraacetyldibenzylhexaazaisowurtzitane [crystal deposition yield: 85%, purity: 97% (determined by HPLC)].

EXAMPLE 11

[Distillative crystal deposition of $WA_6$ obtained by the reactions of the reaction scheme:$WB_6 \rightarrow WA_4B_2 \rightarrow WA_4H_2 \rightarrow WA_6$] [first solvent: acetic acid; second solvent: diethylene glycol dimethyl ether]

Substantially the same procedure as described in Example 3 was repeated except that, as the reaction solvent for the first-stage reaction, diethylene glycol dimethyl ether was used, that the reaction time for the first-stage reaction was changed to 10 hours, and that, as a first solvent which was added to the reaction system at a point in time between the first-stage reaction and the second-stage reaction, acetic acid was used. The resultant reaction mixture was taken out from the autoclave and the catalyst contained in the reaction mixture was filtered off to thereby obtain a solution as a filtrate. 2.0 g of acetyl chloride was added to the solution and stirred at 40° C. for 1 hour. The resultant reaction mixture was subjected to distillative crystal deposition in substantially the same manner as described in Example 3, to thereby obtain crystals of hexaacetylhexaazaisowurtzitane in a yield of 64%, based on the hexabenzylhexaazaisowurtzitane [crystal deposition yield: 85%; purity: 98% (determined by HPLC)].

EXAMPLE 12

[Distillative crystal deposition of $WA_4F^r_2$ obtained by the reactions of the reaction scheme: $WB_6 \rightarrow WA_4B_2 \rightarrow WA_4F^r_2$] (first solvent: formic acid; second solvent: diethylene glycol diethyl ether)

Substantially the same procedure as in Example 3 was repeated except that, as the reaction solvent for the first-stage reaction, diethylene glycol diethyl ether was used instead of DMAc; that the reaction time for the first-stage reaction was changed from 1 hour to 10 hours; that, as a first solvent which was added to the reaction system at a point in time between the first-stage reaction and the second stage reaction, formic acid was used instead of water; that the second-stage reaction was performed in an atmosphere of nitrogen gas instead of hydrogen gas; and that the reaction time for the second-stage reaction was changed from 1 hour to 5 hours. The formic acid added to the reaction system at a point in time between the first-stage reaction and the second stage reaction has the following 4 functions:

(1) a function as a formylating agent (a function to formylate the N—H groups in the tetraacetylhexaazaisowurtzitane produced during the second-stage reaction to thereby produce tetraacetyldiformylhexaazaisowurtzitane);

(2) a function as a solvent for dissolving tetraacetyldiformylhexaazaisowurtzitane;

(3) a function as a reducing agent (by virtue of this function of the formic acid, the second-stage reaction need not be conducted in an atmosphere of hydrogen gas); and (4) a function as the first solvent which is to be distilled during the distillative crystal deposition.

The reaction mixture obtained by the second-stage reaction was taken out from the autoclave and the catalyst contained in the reaction mixture was filtered off to thereby obtain a solution as a filtrate. The solution was subjected to distillative crystal deposition in substantially the same as in Example 3 to thereby obtain tetraacetyldiformylhexaazaisowurtzitane in a yield of 68%, based on the hexabenzylhexaazaisowurtzitane [crystal deposition yield: 97%; purity: 98% (determined by HPLC)].

EXAMPLE 13

[Distillative crystal deposition of $WA_4F^r_2$ obtained by the reactions of the reaction scheme: $WA_4B_2 \rightarrow WA_4F^r_2$] (first solvent: formic acid; second solvent: ethylene glycol diethyl ether)

Substantially the same procedure as in Example 5 was repeated except that, as the reaction solvents, 30 ml of formic acid and 30 ml of ethylene glycol diethyl ether were used; that the reaction was performed in an atmosphere of nitrogen gas instead of hydrogen gas; that the reaction time was changed from 1 hour to 3 hours; and that the reaction temperature was changed from 90° C. to 80° C. As a result, tetraacetyldiformylhexaazaisowurtzitane was obtained in a yield of 95%, based on the tetraacetyldibenzylhexaazaisowurtzitane [crystal deposition yield: 98%; purity: 98% (determined by HPLC)].

Example 14

[Synthesis of $WA_4H_2$, in which the by-produced carboxylic acid was removed by azeotropic distillation] [$WB_6 \rightarrow WA_4B_2 \rightarrow$(azeotropic distillation)$\rightarrow WA_4H_2$] (first solvent: water; second solvent: DMAc)

The first-stage reaction was performed in the same manner as in Example 3 to thereby obtain a reaction mixture containing tetraacetyldibenzylhexaazaisowurtzitane. The obtained reaction mixture was taken out from the autoclave and then subjected to filtration to remove the catalyst. To the resultant filtrate was added 60 ml of toluene to obtain a mixture. Using a distillation column having its bottom connected to a still, the obtained mixture was subjected to distillation to remove acetic acid together with the toluene by azeotropic distillation. As a result, a DMAc solution containing approximately 30 ml of toluene was obtained in the still. Then, the DMAc solution was subjected to distillation to distill off the toluene. The resultant DMAc solution had an acetic acid concentration of 2% or less.

The above-mentioned DMAc solution, 0.84 g of 10% Pd—C (as a catalyst) which had been reduced with hydrazine prior to use and 30 ml of water were charged into a 100 ml autoclave and the autoclave was closed. The autoclave was purged with nitrogen gas. Then, hydrogen gas was introduced into the autoclave so that the internal pressure of the autoclave became 9 kgf/cm². Subsequently, the stirring of the DMAc solution in the autoclave was started at a stirring rate of 700 rpm, and the temperature in the autoclave was elevated to 90° C. to perform a reaction. The reaction was continued for 1 hour after the temperature in the autoclave became 90° C. After completion of the reaction, the resultant reaction mixture was taken out from the autoclave and subjected to filtration to remove the catalyst. The resultant filtrate was subjected to distillative crystal deposition in substantially the same manner as in Example 3 to thereby obtain a mixture containing tetraacetylhexaazaisowurtzitane [yield: 76%; purity: 98% (determined by HPLC); crystal deposition yield: 98%].

In this process, since the content of acetic acid in the mixture obtained by the distillative crystal deposition is 2% or less, the recycling of DMAc can be easily conducted simply by subjecting the mixture to redistillation (since acetic acid causes a skeletal decomposition of the hexabenzylhexaazaisowurtzitane used as a starting material, a solvent containing a large mount of acetic acid cannot be used as a solvent for the first-stage reaction).

EXAMPLE 15

[Synthesis of $WA_4H_2$, in which the by-produced carboxylic acid was removed by azeotropic distillation] [Reaction route: $WB_6 \rightarrow WA_4B_2 \rightarrow WA_4H_2 \rightarrow$(azeotropic distillation)] (first solvent: water; second solvent: DMAc)

The first-stage and second-stage reactions were performed in substantially the same manner as in Example 3 to obtain a reaction mixture. The obtained reaction mixture was taken out from the autoclave and then subjected to filtration to remove the catalyst. The resultant mixture was subjected to distillative crystal deposition in substantially the same manner as in Example 3 to thereby obtain a mixture containing tetraacetylhexaazaisowurtzitane [yield: 79%; purity: 97% (determined by HPLC); crystal deposition yield: 94%].

To the mixture obtained by the distillative crystal deposition was added 60 ml of toluene and the resultant mixture was subjected to distillation to remove acetic acid by azeotropic distillation. As a result, a DMAc solution containing about 30 ml of toluene was obtained in the still. The obtained DMAc solution was subjected to redistillation to remove toluene. The resultant DMAc solution had an acetic acid concentration of 2% or less.

EXAMPLES 16 THROUGH 20

[Experiments to demonstrate the advantage achieved by the use of an amide group-containing organic solvent in the reaction of the reaction scheme: $WB_6 \rightarrow WA_nB_{(6-n)}$ (n is an integer of 4 or 5)]

Experiments were conducted to evaluate the influence of the acidity and basicity of a reaction solvent on the reaction of the reaction scheme: $WB_6 \rightarrow WA_nB_{(6-n)}$, using as reaction solvents acetic acid (AcOH: acidic solvent), ethylbenzene (EB: neutral solvent), N,N-Dimethylacetamide (DMAc: weakly basic solvent), 1,3-dimethyl-2-imidazolidone (DMI: weakly basic solvent) and N,N-Dimethylaniline (DMA: basic solvent), respectively. Each of the experiments was conducted as follows.

0.118 g (0.167 mmol) of hexabenzylhexaazaisowurtzitane, 0.106 g of 10% Pd—C (as a catalyst), 0.859 g (9.00 mmol) of acetic anhydride, and 10 ml of a reaction solvent were charged into a 300 ml pressure tube (made of SUS stainless steel). The pressure tube was purged with nitrogen gas. Then, hydrogen gas was introduced into the tube so that the internal pressure of the tube became 2 kgf/cm$^2$. The tube was set in a shaker having a temperature of 60° C., and the shaking was conducted at a shaking rate of 90 to 100 spm for 4 hours to thereby perform a reaction. After completion of the reaction, the resultant reaction mixture was taken out from the tube and subjected to analysis by GC. Results are shown in Table 3.

As is apparent from Table 3, when a reaction is performed using a weakly basic, amide group-containing organic solvent, such as DMAc or DMI, the occurrence of the skeletal decomposition is suppressed and the yield of compounds having hexaazaisowurtzitane skeleton is high, as compared to those in the case where a reaction is performed using an acidic solvent, such as AcOH, or a neutral solvent, such as EB. Further, when a reaction is performed using a basic solvent, such as DMA, substantially no skeletal decomposition occurs; however, the reaction activity is too low, so that only $WA_2B_4$, which is an intermediate compound formed at an early stage of the reaction of the reaction scheme: $WB_6 \rightarrow WA_nB_{(6-n)}$, is obtained.

EXAMPLES 21 THROUGH 24

In these Examples, experiments were conducted to show that even if the reaction: $WB_6 \rightarrow WA_nB_{(6-n)}$ is performed at a high temperature, the use of a weakly basic, amide group-containing organic solvent in such a reaction enables the skeletal decomposition to be suppressed. Experiments were conducted as follows.

0.118 g (0.167 mmol) of hexabenzylhexaazaisowurtzitane, 0.106 g of 10% Pd—C (as a catalyst), 0.510 g (5.00 mmol) of acetic anhydride, and 10 ml of DMAc were charged into a 300 ml pressure tube (made of SUS stainless steel). The tube was purged with nitrogen gas. Then, hydrogen gas was introduced into the tube so that the internal pressure of the tube became 2 kgf/cm$^2$. The tube was set in a shaker and the shaking was conducted at a shaking rate of 100 to 110 spm for 4 hours at a varied constant temperature. After completion of the reaction, the resultant reaction mixture was taken out from the tube and subjected to analysis by GC. Results are shown in Table 4.

TABLE 3

| Example No. | Solvent | *1 Toluene (mmol) | *2 N-acetyl-benzyl-amine (mmol) | $WA_2B_4$ (mmol) | $WA_3B_3$ (mmol) | $WA_4B_2$ (mmol) | $WA_5B_1$ (mmol) | $WA_4E_2$ (mmol) | $WA_3E_3$ (mmol) | *3 W-skeleton (mmol) |
|---|---|---|---|---|---|---|---|---|---|---|
| 16 | AcOH | 0.37 | 0.30 | 0.002 | 0.003 | 0.003 | 0 | 0 | 0 | 0.008 |
| 17 | EB | 0.75 | 0.00 | 0.000 | 0.045 | 0.060 | 0.009 | 0 | 0 | 0.144 |
| 18 | DMAc | 0.85 | 0.00 | 0.000 | 0.000 | 0.050 | 0.056 | 0.031 | 0.029 | 0.166 |
| 19 | DMI | 0.92 | 0.00 | 0.000 | 0.000 | 0.020 | 0.047 | 0.075 | 0.020 | 0.167 |
| 20 | DMA | 0.35 | 0.00 | 0.164 | 0.000 | 0.000 | 0.000 | 0.000 | 0.000 | 0.164 |

The units for all of the amounts in Table 3 are mmol.
B represents a benzyl group;
A represents an acetyl group; and
E represents an ethyl group.
*1: A compound derived from benzyl groups by debenzylation reaction. The formation amount of toluene indicates the degree of advancement of the reaction.
*2: A compound generated by acetylation of benzylamine, wherein the benzylamine is a product of the skeletal decomposition of $WB_6$ by the acidic protons produced. The formation amount of this compound indicates the degree of advancement of the skeletal decomposition.
*3: Total amount of the compounds having hexaazaisowurtzitane skeleton, which total amount is detected by gas chromatography. This total amount contains the amounts of hexaazaisowurtzitane derivatives which are not shown in Table 3.

TABLE 4

| Example No. | Temperature (° C.) | Time (hour) | *1 Toluene (mmol) | $WA_2B_4$ (mmol) | $WA_3B_3$ (mmol) | $WA_4B_2$ (mmol) | $WA_5B_1$ (mmol) | $WA_4E_2$ (mmol) | $WA_3E_3$ (mmol) | *2 W-Skeleton (mmol) |
|---|---|---|---|---|---|---|---|---|---|---|
| 21 | 165 | 2 | 0.86 | 0.000 | 0.040 | 0.071 | 0.034 | 0.019 | 0.000 | 0.164 |
| 22 | 150 | 0.5 | 0.89 | 0.000 | 0.005 | 0.057 | 0.043 | 0.000 | 0.000 | 0.165 |
| 23 | 110 | 2 | 0.91 | 0.000 | 0.000 | 0.041 | 0.041 | 0.000 | 0.000 | 0.167 |
| 24 | 80 | 0.5 | 0.85 | 0.000 | 0.000 | 0.050 | 0.051 | 0.048 | 0.017 | 0.166 |

In Table 4,
B represents a benzyl group;
A represents an acetyl group; and
E represents an ethyl group.
*1: A compound derived from benzyl groups by debenzylation reaction. The formation amount of toluene indicates the degree of advancement of the reaction.
*2: Total amount of the compounds having hexaazaisowurtzitane skeleton, which total amount is detected by gas chromatography. This total amount contains the amounts of hexaazaisowurtzitane derivatives which are not shown in Table 4.

As is apparent from Table 4, the use of a weakly basic, amide group-containing organic solvent as a reaction solvent is advantageous in that even when a reaction is performed under high temperature conditions (up to 165° C.), almost no skeletal decomposition occurs.

As a comparative experiment, substantially the same procedure as in Example 7 was repeated, except that EB was used as a reaction solvent. As a result, the yield of compounds having the hexaazaisowurtzitane skeleton was only 60% or less (0.100 mmol or less).

EXAMPLE 25

In this Example, an experiment was conducted to show that if a reaction solvent containing an AcOH in an amount of about 5% by weight or less, based on the weight of the reaction solvent, is used in the reaction of the reaction scheme: $WB_6 \rightarrow WA_nB_{(6-n)}$, the AcOH contained in the reaction solvent in such a small amount does not have any unfavorable influence on the reaction.

The first-stage reaction was performed in substantially the same manner as in Example 3, except that 1.5 ml of acetic acid was added to the DMAc (reaction solvent), and that the reaction time was changed to 2 hours.

As a result, the yields of tetraacetyldibenzylhexaazaisowurtzitane and tetraacetylhexaazaisowurtzitane, based on the hexabenzylhexaazaisowurtzitane, were 52% and 21%, respectively.

EXAMPLE 26

In this Example, an experiment was conducted to show that even if the first-stage reaction is conducted using the $WB_6$ in an amount as large as about 14% by weight, based on the weight of a reaction solvent, the first-stage reaction proceeds.

The first-stage reaction was performed in substantially the same manner as in Example 3, except that the amounts of hexabenzylhexaazaisowurtzitane and 10% Pd—C was were changed to 4.2 g and 2.1 g, respectively, and that the reaction time was changed to 40 minutes.

As a result, the yields of tetraacetyldibenzylhexaazaisowurtzitane and tetraacetylhexaazaisowurtzitane, based on the hexabenzylhexaazaisowurtzitane, were 53% and 19%, respectively.

EXAMPLE 27

To 5.0 g of a viscous slurry containing 56.8% by weight of tetraacetylhexaazaisowurtzitane obtained in the same manner as in Example 2 was added 150 ml of water and 100 ml of chloroform, followed by stirring to thereby dissolve the slurry. The resultant solution was allowed to stand to form a chloroform layer and an aqueous layer. Then, the aqueous layer was taken out and subjected to distillation under reduced pressure to remove a liquid component to thereby obtain 2.26 g of tetraacetylhexaazaisowurtzitane in dry form [crystal deposition yield: 80%; purity: 95% (determined by HPLC)].

INDUSTRIAL APPLICABILITY

The method of the present invention is commercially advantageous in that it can be used for producing an acyl group-containing hexaazaisowurtzitane derivative in high purity form in high yield and at low cost, wherein the hexaazaisowurtzitane derivative is useful as a precursor of a hexanitroisowurtzitane derivative which can be used for improving the performance of conventional explosives.

What is claimed is:

1. A method for producing a tetraacylhexaazaisowurtzitane, which comprises:

(I) providing a composition system comprising:
a mixed solvent (a) of at least one first solvent selected from the group consisting of water and carboxylic acids and at least one second solvent selected from the group consisting of organic solvents excluding carboxylic acids, and
a tetraacylhexaazaisowurtzitane (b) represented by the following formula (3):

$$WA_4H_2 \qquad (3)$$

wherein each A independently represents an acyl group having 1 to 10 carbon atoms, H represents a hydrogen atom, and W represents a hexavalent hexaazaisowurtzitane residue represented by the following formula (2):

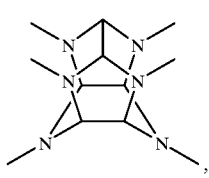

(2)

at least a part of said tetraacylhexaazaisowurtzitane (b) being dissolved in said mixed solvent (a);

(II) removing at least a part of said first solvent from said composition system to deposit crystals of said tetraacylhexaazaisowurtzitane (b); and (III) isolating the deposited crystals from said composition system.

2. The method according to claim 1, wherein said tetraacylhexaazaisowurtzitane (b) is a product obtained by a synthesis process using at least one reaction solvent.

3. The method according to claim 2, wherein said at least one reaction solvent is the same as at least one solvent selected from the group consisting of said first solvent and said second solvent, and
wherein, in said composition system provided in step (I), at least one solvent selected from the group consisting of said first solvent and said second solvent is derived from said at least one reaction solvent.

4. The method according to claim 1, wherein said second solvent has a boiling point which is higher than that of said first solvent, and the removal of at least a part of said first solvent from said composition system is performed by distillation.

5. The method according to claim 3, wherein said second solvent has a boiling point which is higher than that of said first solvent, and the removal of at least a part of said first solvent from said composition system is performed by distillation.

6. The method according to claim 5, wherein said tetraacylhexaazaisowurtzitane (b) is obtained by a synthesis process using at least two reaction solvents,
wherein said at least two reaction solvents are the same as said at least one first solvent and said at least one second solvent,
wherein, in said composition system provided in step (I), said at least one first solvent and said at least one second solvent are derived from said at least two reaction solvents, and wherein said at least one first solvent is selected from the group consisting of water and acetic acid and said at least one second solvent is selected from the group consisting of organic solvents having a boiling point which is higher than that of water when said first solvent is water or having a boiling point which is higher than that of acetic acid when said first solvent is acetic acid or a mixture of water and acetic acid.

7. The method according to claim 5, wherein said tetraacylhexaazaisowurtzitane (b) is obtained by a synthesis process using at least two reaction solvents,
wherein said at least two reaction solvents are the same as said at least one first solvent and said at least one second solvent,
wherein, in said composition system provided in step (I), said at least one first solvent and said at least one second solvent are derived from said at least two reaction solvents, and
wherein said first solvent is water and said at least one second solvent is selected from the group consisting of amide group-containing organic solvents having a compatibility with water and having a boiling point which is higher than that of water.

8. The method according to claim 6, wherein said synthesis process for obtaining said tetraacylhexaazaisowurtzitane (b) comprises subjecting a tetraacylbis(arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for formula (3)
to dearylmethylation in the presence of said at least two reaction solvents.

9. The method according to claim 7, wherein said synthesis process for obtaining said tetraacylhexaazaisowurtzitane (b) comprises subjecting a tetraacylbis(arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for formula (3)
to dearylmethylation in the presence of said at least two reaction solvents.

10. The method according to claim 5, wherein said tetraacylhexaazaisowurtzitane (b) is obtained by a synthesis process using at least two reaction solvents,
wherein said at least two reaction solvents are the same as said at least one first solvent and said at least one second solvent,
wherein, in said composition system provided in step (I), said at least one first solvent and said at least one second solvent are derived from said at least two reaction solvents,
wherein said first solvent is water and said at least one second solvent is selected from the group consisting of amide group-containing organic solvents having a compatibility with water and having a boiling point which is higher than that of water, and
wherein said synthesis process for obtaining said tetraacylhexaazaisowurtzitane (b) comprises the steps of:
 (i) subjecting a hexakis(arylmethyl)hexaazaisowurtzitane to reductive dearylmethylation in the presence of an acylating agent containing acyl group A (wherein A is as defined for formula (3)) to obtain a reaction mixture (i) containing a tetraacylbis(arylmethyl)hexaazaisowurtzitane represented by the following formula (4):

$$WA_4B_2 \qquad (4)$$

wherein each B independently represents an arylmethyl group having 7 to 21 carbon atoms, and each of W and A is as defined above for formula (3) and containing a carboxylic acid and an arylmethane as by-products,
 (ii) adding water to said reaction mixture (i), and
 (iii) subsequently subjecting the resultant mixture to dearylmethylation to thereby produce a reaction mixture (iii) containing a tetraacylhexaazaisowurtzitane of formula (3), while by-producing an arylmethane.

11. The method according to claim 10, wherein said carboxylic acid by-produced in step (i) is removed from said reaction mixture (i) obtained in step (i) by azeotropic distillation together with an arylmethane comprising said arylmethane by-product by-produced in step (i).

12. The method according to claim 10, wherein said carboxylic acid by-produced in step (i) is removed from said composition system, by azeotropic distillation together with an arylmethane comprising said arylmethane by-product by-produced in each of step (i) and step (iii), from said composition system during the removal of said first solvent by distillation in step (II) or from a portion of said composition system which portion remains after said deposited crystals has been isolated from said composition system in step (III).

13. The method according to claim 10, wherein said second solvent is at least one amide group-containing organic solvent selected from the group consisting of N,N-dimethylacetamide, N,N-dimethylformamide, 1,3-dimethyl-2-imidazolidone and N-methyl-2-pyrrolidone.

14. The method according to claim 11, wherein said second solvent is at least one amide group-containing organic solvent selected from the group consisting of N,N-dimethylacetamide, N,N-dimethylformamide, 1,3-dimethyl-2-imidazolidone and N-methyl-2-pyrrolidone.

15. The method according to claim 12, wherein said second solvent is at least one amide group-containing organic solvent selected from the group consisting of N,N-dimethylacetamide, N,N-dimethylformamide, 1,3-dimethyl-2-imidazolidone and N-methyl-2-pyrrolidone.

16. The method according to claim 11, wherein said by-produced carboxylic acid is acetic acid and said arylmethane is toluene.

17. The method according to claim 12, wherein said by-produced carboxylic acid is acetic acid and said arylmethane is toluene.

18. The method according to claim 14, wherein said by-produced carboxylic acid is acetic acid and said arylmethane is toluene.

19. The method according to claim 15, wherein said by-produced carboxylic acid is acetic acid and said arylmethane is toluene.

20. The method according to claim 8 or 9, wherein said tetraacylbis(arylmethyl)hexaazaisowurtzitane represented by formula (4) is obtained by a process comprising subjecting a hexakis(arylmethyl)hexaazaisowurtzitane to reductive dearylmethylation in the presence of an acylating agent containing acyl group A (wherein A is as defined for formula (3)) and amide group-containing organic solvent.

21. The method according to claim 20, wherein said amide group-containing organic solvent is at least one member selected from the group consisting of N,N-dimethylacetamide, N,N-dimethylformamide, 1,3-dimethyl-2-imidazolidone and N-methyl-2-pyrrolidone.

22. A method for producing a tetraacylbis(arylmethyl)hexaazaisowurtzitane represented by the following formula (4):

$$WA_4B_2 \quad (4)$$

wherein each A independently represents an acyl group having 1 to 10 carbon atoms, B represents an arylmethyl group having 7 to 21 carbon atoms, and W represents a hexavalent hexaazaisowurtzitane residue represented by the following formula (2):

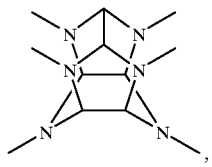

(2)

which comprises subjecting a hexakis(arylmethyl)hexaazaisowurtzitane to reductive dearylmethylation in the presence of an acylating agent containing acyl group A (wherein A is as defined for formula (4)) and an amide group-containing organic solvent, thereby producing a tetraacylbis(arylmethyl)hexaazaisowurtzitane in the form of a mixture thereof with said amide group-containing organic solvent.

23. The method according to claim 22, wherein said amide group-containing organic solvent is at least one member selected from the group consisting of N,N-dimethylacetamide, N,N-dimethylformamide, 1,3-dimethyl-2-imidazolidone and N-methyl-2-pyrrolidone.

24. A method for producing a tetraacylhexaazaisowurtzitane represented by the following formula (3):

$$WA_4H_2 \quad (3)$$

wherein each A independently represents an acyl group having 1 to 10 carbon atoms, H represents a hydrogen atom, and W represents a hexavalent hexaazaisowurtzitane residue represented by the following formula (2):

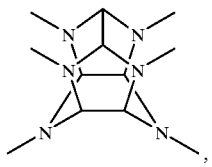

(2)

which comprises subjecting a tetraacylbis(arylmethyl)hexaaza-isowurtzitane represented by the following formula (4):

$$WA_4B_2 \quad (4)$$

wherein each B independently re presents an arylmethyl group having 7 to 21 carbon atoms, and each of W and A is as defined for formula (3)

to reductive dearylmethylation in the presence of an acylating agent containing acyl group A (wherein A is as defined for formula (3)) and a solvent, wherein said solvent comprises a mixture of water and an amide group-containing organic solvent.

25. The method according to claim 24, wherein said tetraacylbis(arylmethyl)hexaazaisowurtzitane is obtained by subjecting a hexakis(arylmethyl)hexaazaisowurtzitane represented by the following formula:

$$WB_6$$

wherein each of W and B is defined above for formula (4) to reductive dearylmethylation in the presence of an acylating agent containing acyl group A (wherein A is as defined for formula (3)) and an amide group-containing organic solvent.

26. The method according to claim 24 or 25, wherein said amide group-containing organic solvent is at least one member selected from the group consisting of N,N-dimethylacetamide, N,N-dimethylformamide, 1,3-dimethyl-2-imidazolidone and N-methyl-2-pyrrolidone.

* * * * *